US009844620B2

(12) United States Patent
Stuva et al.

(10) Patent No.: US 9,844,620 B2
(45) Date of Patent: Dec. 19, 2017

(54) BLOOD SET COMPONENT CONNECTION DETECTION

(71) Applicant: GAMBRO LUNDIA AB, Lund (SE)

(72) Inventors: Rickie L. Stuva, New Hope, MN (US); Steve Fyten, Ramsey, MN (US); John O'Mahony, Maple Grove, MN (US)

(73) Assignee: Gambro Lundia AB, Lund (SE)

( * ) Notice: Subject to any disclaimer, the term of this patent is extended or adjusted under 35 U.S.C. 154(b) by 109 days.

(21) Appl. No.: 14/653,008

(22) PCT Filed: Dec. 16, 2013

(86) PCT No.: PCT/US2013/075385
§ 371 (c)(1),
(2) Date: Jun. 17, 2015

(87) PCT Pub. No.: WO2014/099779
PCT Pub. Date: Jun. 26, 2014

(65) Prior Publication Data
US 2015/0335809 A1    Nov. 26, 2015

Related U.S. Application Data

(60) Provisional application No. 61/739,964, filed on Dec. 20, 2012.

(51) Int. Cl.
*A61M 37/00* (2006.01)
*A61M 1/26* (2006.01)
(Continued)

(52) U.S. Cl.
CPC .............. *A61M 1/267* (2014.02); *A61M 1/14* (2013.01); *A61M 1/367* (2013.01);
(Continued)

(58) Field of Classification Search
CPC .......... A61M 1/14; A61M 1/28; A61M 1/267; A61M 1/367; A61M 1/3641;
(Continued)

(56) References Cited

U.S. PATENT DOCUMENTS 5,795,317 A    8/1998   Brierton
6,044,691 A *   4/2000   Kenley ............... A61M 1/3621
                                                   210/646
(Continued)

FOREIGN PATENT DOCUMENTS

EP          2218470       8/2010
WO    WO 2009/127683   10/2009

OTHER PUBLICATIONS

International Preliminary Examination Report for PCT/US2013/075385 dated Jul. 2, 2015 (9 pages).
(Continued)

*Primary Examiner* — Philip R Wiest
(74) *Attorney, Agent, or Firm* — Mueting, Raasch & Gebhardt, P.A.

(57) ABSTRACT

Extracorporeal blood treatment systems and methods to detect the connection of one or more components (e.g., of an extracorporeal blood set) thereto (e.g., to one or more pressure transducers contained in the system housing) by, for example, controlling an air pump apparatus to provide air to a connection port at which the component is to be connected and monitoring pressure resulting therefrom to detect whether the component is operatively connected (e.g., based on a detected change in the monitored pressure due to the increased resistance, based on a monitored rate of decay of pressure of injected air, etc.).

34 Claims, 20 Drawing Sheets

(51) Int. Cl.
*A61M 1/14* (2006.01)
*A61M 1/36* (2006.01)

(52) U.S. Cl.
CPC ....... *A61M 1/3641* (2014.02); *A61M 2205/07* (2013.01); *A61M 2205/12* (2013.01); *A61M 2205/14* (2013.01); *Y10T 137/0402* (2015.04); *Y10T 137/85986* (2015.04)

(58) Field of Classification Search
CPC ............... A61M 1/3639; A61M 1/3621; Y01T 137/0402; Y01T 137/85986
See application file for complete search history.

(56) References Cited

U.S. PATENT DOCUMENTS

| | | |
|---|---|---|
| 6,280,406 B1 | 8/2001 | Dolecek |
| 6,526,357 B1 | 2/2003 | Soussan |
| 6,821,432 B2 | 11/2004 | Metzner |
| 8,092,414 B2 | 10/2012 | Schnell |
| 8,718,957 B2 | 5/2014 | Furmanski |
| 8,960,810 B2 | 2/2015 | Crnkovich |
| 2004/0223857 A1 | 11/2004 | Kline |
| 2005/0126998 A1 | 6/2005 | Childers |
| 2008/0027368 A1 | 1/2008 | Kollar |
| 2010/0234786 A1 | 9/2010 | Fulkerson |
| 2010/0234787 A1 | 9/2010 | Masaoka |
| 2012/0130338 A1* | 5/2012 | Schnell ............... A61M 1/3639 604/500 |
| 2013/0028788 A1 | 1/2013 | Gronau |

OTHER PUBLICATIONS

International Search Report and Written Opinion for PCT/US2013/075385 dated Mar. 7, 2014 (12 pages).

* cited by examiner

BLOOD SET COMPONENT CONNECTION DETECTION

This application is the U.S. National Stage Application of International Application No. PCT/US2013/075385, filed Dec. 16, 2013 and published in English on Jun. 26, 2014 as International Publication No. WO 2014/099779 A1, which claims the benefit under 35 U.S.C. 119(e) of U.S. Provisional Application No. 61/739,964 filed Dec. 20, 2012; all of which are incorporated herein by reference in their entirety.

BACKGROUND

The disclosure herein relates to extra-corporeal blood treatment. More particularly, the disclosure relates to the connection of an extracorporeal blood set to a machine for extra-corporeal blood treatment (e.g., the connection of tubing, such as a return monitor line, or pressure pods used for measuring pressure of a fluid flowing through the pod).

Extracorporeal blood sets, for example, are used in a variety of medical procedures to treat patients, such as, the infusion of drugs, dialysis, continuous renal replacement therapy (CRRT), extracorporeal membrane oxygenation (ECMO), etc. Reducing cost while maintaining safety and accuracy are of concern in today's healthcare environment. Reducing the number of tasks a user must perform and/or monitoring tasks performed such that the tasks are completed correctly, reduces the cost of operation and increases the quality of health care.

In many extracorporeal blood sets (e.g., disposable blood sets) provided, for example, for use in therapy systems, pressure pods are used to separate the liquid/blood filled disposable extracorporeal circuit from an electronic pressure sensor of the system by preventing liquid ingress and contamination while enabling the transfer and measurement of pressure. Such pressure pods may include a pressure transducer side separated from a fluid flow side by a diaphragm. In one or more configurations, for example, the pressure transducer side of the pressure pod is filled with air in a sealed space providing isolation (e.g., electrical isolation) thereof from the fluid flow side (e.g., liquid flow side) and a medium for the transfer of pressure from the fluid flow side to the pressure transducer side of the pressure pod, e.g., the compression of air. For example, the diaphragm which separates the pressure transducer side from the fluid flow side of the pressure pod may be flexible and oversized to ensure none of the force exerted by the pressure on the diaphragm in the extracorporeal blood circuit is lost to the tension or compression of the diaphragm. Further, for example, the pressure pod (e.g., the pressure transducer side of the pressure pod) may be operatively connected by tubing (e.g., air filled) to a pressure transducer for sensing pressure at a distance away from the pressure pod (e.g., a pressure transducer located in a system housing upon which the extracorporeal blood set is mounted or a system to which the extracorporeal blood set is connected).

Further, many extracorporeal blood sets may also contain other lines that must be connected to pressure ports to monitor the pressure therein. For example, such disposable sets may contain a return monitor line on the air side of a deaeration chamber that is to be connected to a return pressure port of a system to monitor the pressure in the patient blood return line using a pressure transducer within the system housing.

In other words, for example, each disposable extracorporeal blood set connectable to a treatment system (e.g., mounted on a system housing and connected to one or more pressure transducers therein) may contain multiple pressure pods. Each pressure pod may contain a diaphragm that separates a liquid (e.g., blood in the fluid side of the pressure pod) from an air cavity (e.g., on the transducer side of the pressure pod) and which is configured to fit into a pressure sensor or pod receptacle of the system (e.g., a connection apparatus for mounting the pressure pod on a dialysis unit). The pressure pods and pressure transducers (e.g., inside the control unit or system housing, such as a dialysis unit) enable noninvasive pressure monitoring of the liquid (e.g., blood), since the liquid never comes into contact with the actual pressure transducer. A pressure pod receptacle may provide a connection between the pressure pods and the pressure transducers within the system housing. For example, the pressure pods may be manually attached to the pressure pod receptacle by a user each time a new disposable blood set is installed. The connection between the pressure pod and the pressure pod receptacle must be airtight to yield valid pressure sensor readings by the pressure transducers within the system housing. Likewise, connecting the return monitor line to the return pressure port is also a manual operation. After installation of the pressure pods and connection of the return line, the user is typically requested to indicate via a graphical user interface associated with the system that the pressure pod installation and the return monitor line connection have been completed.

Although user interaction may be used to confirm that the pressure pods and the return monitor line have been connected by the user to the pressure pod receptacle and the return port, respectively, such confirmation by the user does not verify that the pressure pods or return monitor line have been installed correctly by the user. For example, if the user fails to install the pressure pods or does not achieve an airtight connection between the pressure pods and the pressure pod receptacle, such an incorrect installation may not be discovered until later in a machine startup procedure when more general pressure sensing alarms may be triggered. Isolating the cause of more general pressure sensing alarms may be difficult. Further, pressure sensor readings from a pressure pod that is not installed or is incorrectly installed would typically be invalid. Still further, if the user fails to connect the return monitor line to the return pressure port before proceeding with setup, then return pressure readings may be near zero resulting in incorrect operation and potential damage to a disposable set or other control unit components.

SUMMARY

The present disclosure describes systems and methods which provide for detection of the operative connection of components (e.g., pressure pods, lines, etc.) to a system (e.g., connection to a system housing, such as by way of connection apparatus). For example, in one or more embodiments, the present disclosure provides for the independent verification that the components are correctly installed (e.g., verification of correct installation such that valid pressure readings are attainable as opposed to just the user indicating on a graphical user interface that a component is installed). Further, for example, in one or more embodiments, the present disclosure may provide for an automated sequence to monitor and detect the correct installation of various components, including, for example, pressure pods and return pressure monitor lines.

One exemplary embodiment of an extracorporeal blood treatment system according to the present disclosure includes an air pump apparatus, one or more pressure transducers, a controller operatively coupled to the air pump apparatus and the one or more pressure transducers, and a system housing to contain at least the air pump apparatus, the controller, and the one or more pressure transducers. Further, the system may include an extracorporeal blood set (e.g., including a plurality of components configured to be mounted on, for example, coupled to, the system housing of the extracorporeal blood treatment system using connection apparatus, wherein the connection apparatus may include one or more ports to connect the one or more pressure transducers contained in the system housing to one or more components of the plurality of components of the extracorporeal blood set when mounted on the system housing). The controller may be configured to control the air pump apparatus to provide air to at least one port of the one or more ports and within at least a portion of one or more components when mounted on (e.g., coupled to) the system housing using the connection apparatus and monitor air pressure resulting from the provision of air to the at least one port using at least one of the one or more pressure transducers to detect whether one or more components of the plurality of components are operatively connected to the system housing.

In one or more embodiments of the system, the extracorporeal blood set may include one or more components which include a closed container portion mountable on the system housing of the extracorporeal blood treatment system (e.g., the closed container portion may be operatively connectable to at least one of the one or more pressure transducers). The controller may be configured to control provision of air from the air pump apparatus to at least one port of the one or more ports and within the closed container portion of at least one component when mounted on the system housing using the connection apparatus (e.g., wherein the at least one component creates an increase in resistance to the air provided when mounted on the system housing) and monitor air pressure resulting from the provision of air to the at least one port to determine whether the component comprising the closed container portion is operatively connected to the system housing based on a detected rise in the monitored pressure due to the increased resistance.

For example, the extracorporeal blood set may include a plurality of pressure measurement apparatus configured to be mounted on the system housing of the extracorporeal blood treatment system (e.g., each of the one or more pressure measurement apparatus may include a pressure pod body configured to be mounted on the system housing and a diaphragm separating a fluid side cavity and a transducer side air cavity, wherein the transducer side air cavity may be operatively connectable to at least one of the one or more pressure transducers such that pressure of fluid when present in the fluid side cavity is transferred to the transducer side air cavity via the diaphragm and measureable using the at least one pressure transducer). Further, for example, the controller may be configured to control provision of air from the air pump apparatus to at least one port of the one or more ports and into the transducer side air cavity of a first pressure measurement apparatus of the plurality of pressure measurement apparatus when mounted on the system housing and monitor air pressure resulting from the provision of air to the at least one port to detect whether the first measurement apparatus is operatively connected to the system housing based on a detected rise in the monitored pressure.

For example, in one or more embodiments, the controller may be configured to detect a rise in pressure by comparing the resulting air pressure to a predetermined pressure threshold and determining that the first pressure measurement apparatus is operatively connected if a predetermined number of samples thereof satisfy the predetermined pressure threshold and/or the controller may be configured to detect a rise in pressure by monitoring pressure at the at least one port prior to and after providing air thereto to detect a pressure difference.

Further, in one or more embodiments of the system, the extracorporeal blood set may include an open line element configured to be mounted on the system housing of the extracorporeal blood treatment system and connectable to a port of the one or more ports of the connection apparatus (e.g., the open line element may be operatively connected to at least one of the one or more pressure transducers when mounted on the system housing). The controller may be configured to control injection of air to the port of the one or more ports using the air pump apparatus and within the open line element when mounted on the system housing (e.g., wherein the open line element creates an increase in resistance to the injected air when mounted on the system housing resulting in a decreased rate of decay of the pressure of the injected air) and monitor a rate of decay of pressure of the injected air to determine whether the open line element is operatively connected to the system housing.

For example, the controller may be configured to monitor the rate of decay of pressure by determining a pressure difference integral of the injected air over a period of time following the injection of pressurized air to the port by integrating a difference between the pressure when air is being injected to the port and an initial pressure prior to air being injected to the port, comparing the pressure difference integral to a predetermined pressure integral threshold, and detecting that the open line element is operatively connected if the pressure difference integral satisfies the predetermined pressure integral threshold.

In another embodiment of an extracorporeal blood treatment system, the system may include an air pump apparatus, one or more pressure transducers, a controller operatively coupled to the air pump apparatus and the one or more pressure transducers, and a system housing to contain at least the air pump apparatus, the controller, and the one or more pressure transducers. The system may further include an extracorporeal blood set including a plurality of components, wherein the plurality of components include a plurality of pressure measurement apparatus configured to be mounted on the system housing of the extracorporeal blood treatment system (e.g., each of the one or more pressure measurement apparatus may include a pressure pod body configured to be mounted on the system housing and a diaphragm separating a fluid side cavity and a transducer side air cavity, wherein the transducer side air cavity may be operatively connectable to at least one of the one or more pressure transducers such that pressure of fluid when present in the fluid side cavity is transferred to the transducer side air cavity via the diaphragm and measureable using the at least one pressure transducer). The controller of the system may be configured to control the air pump apparatus to provide a positive air flow from the air pump apparatus to at least one port of the one or more ports into the transducer side air cavity of a pressure measurement apparatus of the plurality of pressure measurement apparatus when mounted on the system housing or provide a negative air flow from at least one port of the one or more ports opposite the positive air flow and may be configured to monitor air pressure resulting from the provision of air by the air pump to detect whether the pressure measurement apparatus is operatively connected to the system housing based on a detected change in the pressure magnitude.

Still further, in one or more embodiments of a system, the system may include a clarifying air filter connected between the air pump apparatus and the one or more ports. Yet further, in one or more embodiments, the system may further include a plurality of valves, wherein the controller may be configured to operate a different valve for each component of the plurality of components to be mounted on the system housing to allow air from the air pump apparatus to be provided for use in detecting whether each respective component of the plurality of components to be mounted has been operatively connected.

Further, in one or more embodiments of a system, the plurality of components of the extracorporeal blood set may include at least a predetermined number of pressure measurement apparatus to be operatively connected to the one or more pressure transducers. The controller may be further configured to detect, during a period of time, whether each of the predetermined number of pressure measurement apparatus has been operatively connected and alert a user if all of the predetermined number of pressure measurement apparatus have not been operatively connected during the period of time.

Still further, one or more embodiments of a system may include a user interface, wherein the controller may be further configured to automatically instruct a user, via the user interface, to perform another task upon detecting that a first component of the one or more components is operatively connected. Further, for example, the controller may be configured to automatically instruct a user, via the user interface, to attach one or more additional components of the plurality of components and, respectively, detect whether each of the one or more additional components are operatively connected to the system housing upon detecting that a first component of the one or more components is operatively connected.

One exemplary embodiment of a method of connecting one or more components of an extracorporeal blood set to a housing of an extracorporeal blood treatment system (e.g., wherein the system housing may contain one or more pressure transducers and an air pump apparatus, wherein the system may include connection apparatus which includes one or more ports to connect the one or more pressure transducers to the one or more components of the extracorporeal blood set, etc.) may include providing an extracorporeal blood set which includes a plurality of components configured to be mounted on the system housing of the extracorporeal blood treatment system, instructing a user, via a user interface, to connect a first component of the plurality of components, providing air generated by the air pump apparatus to at least one of the one or more ports for use in determining whether the first component is operatively connected to the system housing via the at least one port such that a pressure associated with the first component is measureable using at least one of the one or more pressure transducers, and automatically instructing a user, via the user interface, to perform another task upon detecting that the first component is operatively connected.

In one or more embodiments of the method, providing the extracorporeal blood set may include providing one or more components that include a closed container portion mountable on the system housing of the extracorporeal blood treatment system (e.g., wherein the closed container portion is operatively connectable to at least one of the one or more pressure transducers). Further, providing air generated by the air pump apparatus may include controlling provision of air from the air pump apparatus to at least one port of the one or more ports and within the closed container portion of at least one component when mounted on the system housing using the connection apparatus and monitoring air pressure resulting from the provision of air to the at least one port to determine whether the component including the closed container portion is operatively connected to the system housing based on a detected rise in the monitored pressure.

For example, the one or more components including the closed container portion may be a plurality of pressure measurement apparatus configured to be mounted on the system housing of the extracorporeal blood treatment system such as provided herein and the providing air generated by the air pump apparatus may include providing air from the air pump apparatus to at least one port of the one or more ports and into the transducer side air cavity of a first pressure measurement apparatus of the plurality of pressure measurement apparatus when mounted on the system housing. Air pressure resulting from the provision of air to the at least one port may be monitored to detect whether the first measurement apparatus is operatively connected to the system housing based on a detected rise in the monitored pressure.

Further, in one or more embodiments of the method, determining whether the first component is operatively connected to the system housing may include detecting a rise in pressure if the first component is operatively connected to the system housing. Detecting a rise in pressure if the first pressure measurement apparatus is operatively connected to the system housing may include comparing the pressure to a predetermined pressure threshold and determining that the first component is operatively connected if a predetermined number of samples of the resulting air pressure satisfy the predetermined pressure threshold.

Further, in one or more embodiments of the method, providing the extracorporeal blood set may include providing an open line element configured to be mounted on the system housing of the extracorporeal blood treatment system and connectable to a port of the one or more ports of the connection apparatus (e.g., the open line element may be operatively connected to at least one of the one or more pressure transducers when mounted on the system housing). Further, providing air generated by the air pump apparatus may include controlling injection of air to the port of the one or more ports using the air pump apparatus and within the open line element when mounted on the system housing and monitoring a rate of decay of pressure of the injected air to determine whether the open line element is operatively connected to the system housing.

Still further, in one or more embodiments of the method, automatically instructing a user, via the user interface, to perform another task may include instructing a user, via a user interface, to attach one or more additional components of the plurality of components and, respectively, determine whether each of the one or more additional components are operatively connected (e.g., automatically instructing a user, via the user interface, to perform another task without requiring a user to confirm, via the user interface, that the first component is operatively connected).

Yet further, in one or more embodiments, the method may further include operating a different valve for each component of the plurality of components to be mounted on the system housing to allow air from the air pump apparatus to be used for determining whether each respective component of the plurality of components to be mounted has been operatively connected.

Another exemplary embodiment of a method of connecting one or more pressure measurement apparatus of an extracorporeal blood set to a housing of an extracorporeal system (e.g., wherein the system housing contains one or more pressure transducers and an air pump apparatus, and further wherein the system may include connection apparatus that includes one or more ports to connect the one or more pressure transducers to the one or more pressure measurement apparatus of the extracorporeal blood set) may include providing one or more pressure measurement apparatus of an extracorporeal blood set (e.g., wherein each of the one or more pressure measurement apparatus may include a pressure pod body configured to be mounted on the system housing and a diaphragm separating a fluid side cavity and a transducer side air cavity, wherein the transducer side air cavity is operatively connectable to at least one pressure transducer of the one or more pressure transducers such that pressure of fluid when present in the fluid side cavity is transferred to the transducer side air cavity via the diaphragm and measureable by the at least one pressure transducer), providing air generated by the air pump apparatus to a port of the one or more ports and into the transducer side air cavity of a first pressure measurement apparatus when mounted on the system housing, and monitoring air pressure resulting from the provision of air to the port to detect whether the first measurement apparatus is operatively connected to the system housing based on a detected rise in the monitored pressure. For example, detecting a rise in the monitored pressure may include comparing the pressure to a predetermined pressure threshold and determining that the pressure measurement apparatus is operatively connected if a predetermined number of samples of the pressure satisfy the predetermined pressure threshold.

Yet another exemplary embodiment of a method of connecting an open line element of an extracorporeal blood set to a housing of an extracorporeal system (e.g., wherein the system housing contains one or more pressure transducers and an air pump apparatus, and further wherein the system may include connection apparatus that includes at least one port to connect the open line element to at least one pressure transducer of the one or more pressure transducers) may include providing at least one open line element configured to be mounted on the system housing (e.g., wherein the open line element may be operatively connectable to at least one pressure transducer of the one or more pressure transducers such that a pressure therein is measureable using the at least one pressure transducer), controlling injection of pressurized air to the at least one port of the one or more ports using the air pump apparatus and within the open line element when mounted on the system housing, and monitoring a rate of decay of pressure of the injected air to determine whether the open line element is operatively connected to the system housing. For example, monitoring a rate of decay of pressure of the injected air may include determining a pressure difference integral of the injected air over a period of time following the injection of pressurized air to the port, comparing the pressure difference integral to a predetermined pressure integral threshold, and detecting that the open line element is operatively connected if the pressure difference integral satisfies the predetermined pressure integral threshold.

In one or more embodiments of the method, controlling injection of pressurized air to the at least one port may include closing a valve in a line to the at least one port to increase pressure in the line and opening the valve to release pressurized air through the at least one port, and further, for example, determining the pressure difference integral may include integrating the difference between the pressure of air through the port upon release of the pressurized air therethrough and an initial pressure value at the port prior to release of the pressurized air.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
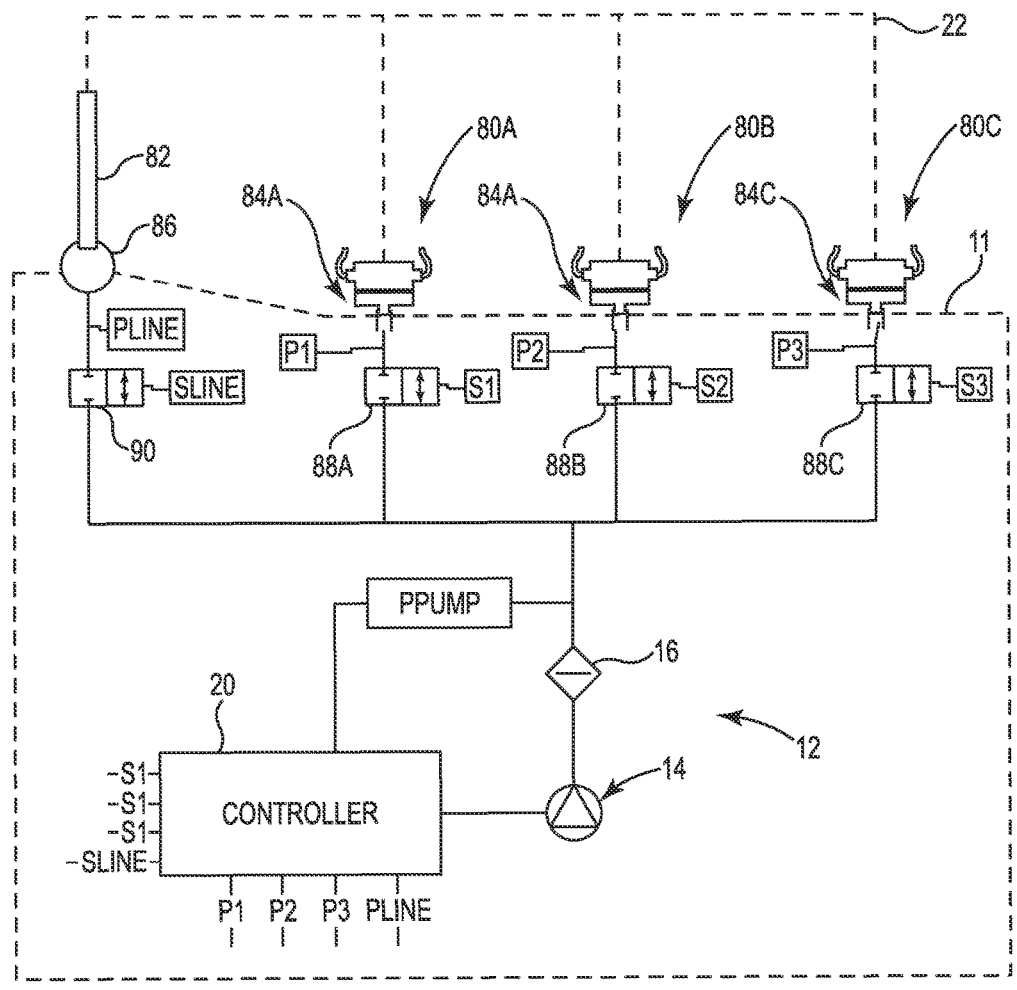
FIG. 1 is a block diagram showing a fluid processing system, such as shown in FIGS. 2-3, including a component connection detection system for detecting connection of components (e.g., pressure pod apparatus and/or lines of an extracorporeal blood set) to components of or within a system housing containing, for example, a controller and/or pressure transducer(s) of the fluid processing system.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods for use in the detecting operative connection of one or more components (e.g., components having a closed container portion, open line elements, etc.) in a fluid processing system (e.g., an extracorporeal blood processing system) shall be described with reference to FIGS. 1-16. For example, in one or more embodiments, such systems and methods may use an air pump apparatus (e.g., automatic repositioning system air pump used to reposition the diaphragm of a pressure pod apparatus) in the monitoring and detection of the operative connection of one or more components to a system housing of the fluid processing system.

Figure 2:
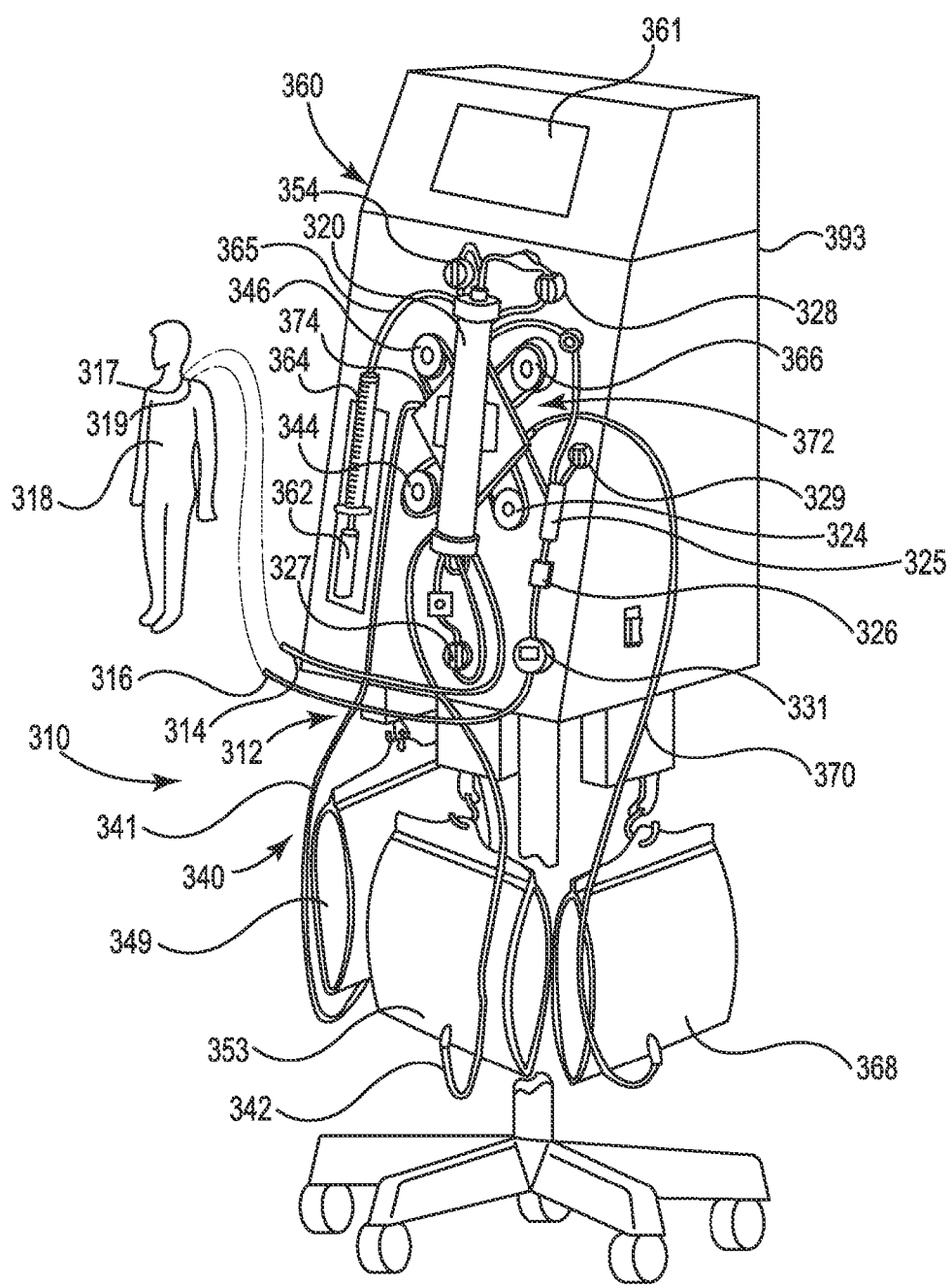
FIG. 2 is a perspective illustration of an exemplary fluid processing system that may include a component connection detection system such as shown generally in FIG. 1.
Figure 3:
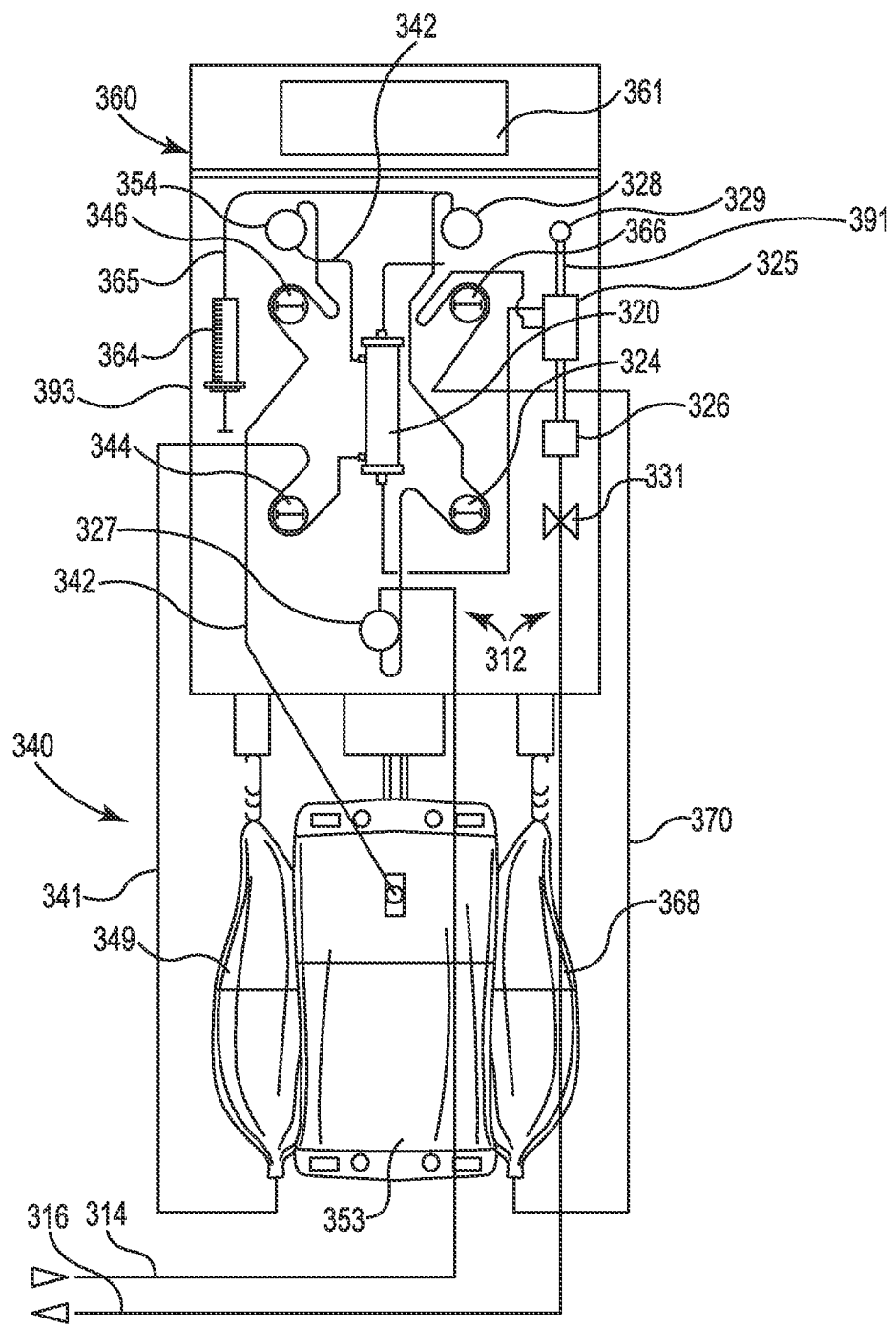
FIG. 3 is a front view of a portion of the exemplary fluid processing system shown in FIG. 2.

FIG. 1 shows a block diagram of an exemplary fluid processing system 10, such as an extracorporeal blood treatment system, shown in FIGS. 2-3, including a component connection detection system 12 for detecting operative connection of one or more components (e.g., of an extracorporeal blood set) to components of the system 10 (e.g., transducers within a system housing). For example, as shown in FIG. 1, the fluid processing system 10 may be an extracorporeal blood treatment system that includes a system housing 11. The component connection detection system 12 may be used to detect whether one or more components of the extracorporeal blood set (e.g., a disposable blood set) are correctly installed such that, for example, valid pressure readings may be obtained during operation of the system 12 (i.e., operative connection) using one or more of such components, as opposed to merely using a user's verification that the one or more components have been connected.

The extracorporeal blood treatment system 10 includes an air pump apparatus 14, one or more pressure transducers (e.g., Pline, P1, P2, P3, and Ppump), and a controller 20 operatively coupled to the air pump apparatus 14 and the one or more pressure transducers (e.g., Pline, P1, P2, P3, and Ppump). An extracorporeal blood set (shown generally as reference number 22) includes a plurality of components (e.g., pressure pod apparatus 80A-80C, deaeration chamber monitor line 82, etc.) configured to be mounted on the system housing 11 of the extracorporeal blood treatment system using connection apparatus (e.g., mating receptacles including one or more ports 84A-84C, return pressure port 86, etc.). The connection apparatus provides for the connection between the one or more pressure transducers (e.g., Pline, P1, P2, P3, and Ppump) contained in the system housing 11 to one or more components (e.g., pressure pod apparatus 80A-80C, deaeration chamber monitor line 82, etc.) of the extracorporeal blood set 22 when mounted on the system housing 11 (e.g., an air or fluid connection for use in sensing pressure).

The controller 20 is configured to control the air pump apparatus 14 to provide air to at least one port of one or more ports of the connection apparatus 84A-84C, 86 (e.g., mating receptacles including one or more ports, return pressure ports, etc.) and within at least a portion of one or more components of the extracorporeal blood set 22 when mounted on the system housing 11 using the connection apparatus. The controller 20 monitors air pressure resulting from the provision of air to the at least one port (e.g., mating receptacles including one or more ports 84A-84C, return pressure port 86, etc.) using at least one of the one or more pressure transducers (e.g., Pline, P1, P2, P3, and Ppump) to detect whether one or more components of the plurality of components (e.g., pressure pod apparatus 80A-80C, deaeration chamber monitor line 82, etc.) are operatively connected to the system housing 11 (i.e., operatively connected such that valid pressure readings may be obtained, for example, during operation or treatment).

The extracorporeal blood set 22 may include various types of components and the present disclosure is not limited to any particular type. For example, such components, for example, may be those used to obtain pressure measurements related to the flow of fluid (e.g., blood) through the lines or tubing of the extracorporeal blood set 22. For example, components of the extracorporeal blood set 22 may include components including a closed container portion (e.g., mountable on the system housing 11 of the fluid processing system 10). A closed container portion may be any closed container portion (of any shape or configuration) into which air may be provided but not allowed to flow therethrough. The closed container portion may be, for example, operatively connected or connectable (e.g., via a port) to at least one of the one or more pressure transducers (e.g., Pline, P1, P2, P3, and Ppump). One exemplary embodiment of such a component including a closed container portion is a pressure pod apparatus having a transducer side air cavity, such as pressure pod apparatus 80A-80C shown in FIG. 1. Such pressure pod apparatus shall be described further herein.

Further, for example, components of the extracorporeal blood set 22 may include components that are open line elements (e.g., mountable on the system housing 11 of the extracorporeal blood treatment system 10). An open line element may be any open element (of any shape or configuration) into which air may be provided but through which air may flow. The open line element may be, for example, operatively connected or connectable (e.g., via a port) to at least one of the one or more pressure transducers (e.g., Pline, P1, P2, P3, and Ppump). One exemplary embodiment of such an open line element is a deaeration chamber monitor line 82 shown in FIG. 1. Such open line elements shall be described further herein.

As described further herein, the techniques for detecting operative connection of components including closed container portions and for detecting connection of open line elements to the system may differ. For example, to detect operative connection of components including closed container portions, generally, a rise in pressure (e.g., pressure magnitude) may be used in detecting operative connection of such components (e.g., a rise in pressure magnitude of a positively provided air flow (wherein the closed container being connected would cause a pressure increase equatable to a magnitude increase) or a rise in pressure magnitude of a negatively provided air flow (wherein the closed container being connected would cause a pressure decrease which is still equatable to a pressure magnitude increase)). For example, when the closed container portion of the component is operatively connected and air is provided therein (e.g., using air pump apparatus 14), the closed container portion acts as an accumulator and pressure will rise as flow is delivered therein. In other words, the closed container portion creates an increase in resistance when operatively connected (e.g., mounted on the system housing 11) relative to a lesser resistance to air provided when the component including the closed container portion is not connected.

Further, for example, to detect operative connection of open line elements, generally, a rate of decay of pressure of air provided is used in detecting operative connection of such components. For example, with the open line element is operatively connected and air (e.g., pressurized air) is injected (e.g., using air pump apparatus 14), the open line element provides a resistance to air flowing therethrough decreasing the rate of decay of pressure. In other words, the rate of decay of the pressure of the air injected (e.g., which is a function of the resistance of the connected open line element) when operatively connected will be decreased relative to the rate of decay of the pressure of the injected air when an open line element is not connected.

The component connection detection functionality described herein may be used in any fluid processing systems that would benefit therefrom. For example, exemplary systems that may benefit from such functionality include systems, generally referred to as dialysis systems. The general term dialysis as used herein includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although extracorporeal blood treatment systems capable of performing general dialysis (as defined above, including TPE) and using component connection detection shall be described herein with reference to the exemplary extracorporeal blood treatment system of FIGS. 2-3, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular fluid processing system.

In the perspective and partial front views of FIGS. 2-3, the exemplary extracorporeal blood treatment system 310 that may implement component connection detection as described herein generally includes a blood tubing circuit 312 having first and second tubing segments 314 and 316 which are both connected to the vascular system of a patient 318 via access and return devices 317 and 319, respectively. Devices 317 and 319 may be cannulas, catheters, winged needles or the like as would be understood by one skilled in the art. Tubing segments 314 and 316 are also connected to a filtration or processing unit 320. In dialysis, filtration unit 320 is a dialyzer, which is also often referred to as a filter. In TPE, it may also be referred to as a plasma filter. In this exemplary system 310, a peristaltic pump 324 is disposed in operative association with the first tubing segment 314. Numerous other component devices of blood circuit 312 are also included as, for example, pressure sensors 327, 328, as well as the tubing clamp 331. Such pressure sensors 327, 328 may be configured as described herein and the detection of the connection of the pressure pod apparatus thereof to the system housing 393 may be implemented as described herein, for example, during setup and operation of system 310.

Also shown in FIGS. 2-3 is the processing fluid or filtrate side of system 310 which generally includes a processing fluid circuit 340 having first and second processing fluid tubing segments 341 and 342. Each of these tubing segments is connected to the filtration unit 320. In these FIGS. 2-3, a respective fluid pump 344, 346 is operatively associated with each of these tubing segments 341 and 342. First tubing segment 341 is also connected to a processing fluid source (e.g., fluid bag 349) which may include electrolytes premixed therein. Second tubing segment 342 is connected to a waste collection device (e.g., a waste container such as a bag 353). A pressure sensor 354 may also be disposed in second dialysis fluid tubing segment 342 (e.g., pressure sensor 354 may be configured as described herein and the detection of the connection of the pressure pod apparatus thereof to the system housing 393 may be implemented as described herein, for example, during setup and operation of system 310).

FIGS. 2-3 show a system which is common as a basic model for numerous dialysis procedures including TPE. Additional fluid lines, circuits, and components may be added (or deleted) to increase treatment options. Further, as shown in FIGS. 2-3, the system 310 includes an extracorporeal blood control apparatus 360 which provides numerous treatment options which are controlled and/or monitored via the control/display screen 361 (e.g., a control apparatus or controller provided in a system housing 393). Touchscreen controls may be incorporated herewith and/or other conventional knobs or buttons (not shown) may be used. Other and more detailed information regarding an example apparatus 360 may be found in U.S. Pat. No. 5,679,245; U.S. Pat. No. 5,762,805; U.S. Pat. No. 5,776,345; and U.S. Pat. No. 5,910,252; inter alia.

A general dialysis treatment procedure as performed, for example, with an apparatus described with reference to FIGS. 2-3 will be generally described for exemplary purposes. First, blood is removed from the patient 318 via access device 317 and flows through access line 314 to the filter 320. Filter 320 processes this blood according to a selected one or more of a number of extracorporeal blood treatment protocols (e.g., selected and controlled via screen interface 361 of control apparatus 360) and then returns the processed or treated blood to the patient 318 through return line 316 and return device 319 inserted in or otherwise connected to the vascular system of the patient 318. The blood flow path to and from the patient 318, which includes the access device 317, the access line 314, the filter 320, as well as the return line 316 and return device 319 back to the patient, forms the blood flow circuit 312.

The pressure sensors may be used to sense various pressures in the system 310. For example, the pressure sensor 327 (e.g., including an access pressure pod apparatus) may be connected in the access line 314 and allow the fluid pressure in the access line 314 to be monitored and the second pressure sensor 328 (e.g., including a filter pressure pod apparatus) may be connected in the blood circuit 312 between the first pump 324 and the blood entrance into the filter 320 and may be used to detect and monitor the pressure of the blood supplied to the entrance of the filter 320.

The system 310 further includes a deaeration chamber 325 in the return line to provide a conveyance path that operates like a vortex to propel air out of the blood. Post-filter replacement solution may be added into the deaeration chamber on the top of the blood to prevent an air/blood interface. A deaeration chamber monitor line 391 connects the deaeration chamber 325 to an internal pressure transducer within the system housing 393 using a connection apparatus, such as, for example, a return pressure port 329. This enables return pressure monitoring, and removal of air from the deaeration chamber, if needed. A fluid barrier at the end of the line protects the interior of the system 310 from fluid entry. A return clamp 331 connected in the blood circuit 312 selectively allows or terminates the flow of blood through the blood circuit 312 (e.g., return clamp 331 may be activated whenever air is detected in the blood by bubble detector 326). Further, a pump 362 may be connected to an anticoagulant container 364 to deliver anticoagulant through an anticoagulant line 365 to the blood in tubing segment 314 and a pump 366 may deliver replacement fluid from a replacement fluid container or bag 368 through a replacement fluid line 370.

The secondary flow circuit 340 is also shown in FIGS. 2-3 as it interacts with filter 320. The secondary flow circuit 340 is connected to the secondary chamber of filter 320. Matter extracorporeally removed from the blood is removed from the secondary chamber of filter 320 through the outlet tubing segment 342 of the secondary flow circuit 340, and matter extracorporeally added to the blood is moved into filter 320 through inlet tubing segment 341 of the secondary flow circuit 340. The secondary flow circuit 340 generally includes the fluid source such as bag 349, inlet fluid line 341, third peristaltic pump 344, the secondary chamber of the filter 320, a waste fluid line 342, pressure sensor 354, fourth pump 346, and the waste collection device such as container 353. The source fluid bag 349 contains a sterile processing fluid, generally isotonic to blood, into which blood impurities will diffuse through the semi-permeable membrane of the filtration unit 320. The pump 344 is connected in inlet fluid line 341 for delivering processing fluid from the processing fluid source 349 into an entrance to the filter 320. The waste collection container 353 is provided to collect or receive matter from the blood transferred across the semi-permeable membrane in filter 320 and/or to receive the used processing fluid after it has passed through the filter 320. The fourth pump 346 is connected to the waste collection line 342 for moving body fluid from the filter 320 into the waste collection container 353. The pressure sensor 354 may also be located in the waste collection line 342 for the purpose of monitoring the pressure in the secondary chamber of filter 320.

The filtration unit 320, the flow tubing lines, and the other components in the primary and secondary flow circuits 312 and 340 described herein (with the exception, for example, of the pumps and perhaps a few other items) may be formed as an integral, replaceable unit (e.g., an extracorporeal blood set). An example of such an integral replaceable unit is described in greater detail in U.S. Pat. No. 5,441,636 entitled Integrated Blood Treatment Fluid Module (see also, U.S. Pat. No. 5,679,245, entitled Retention Device for Extracorporeal Treatment Apparatus). The component connection detection algorithms described herein may be used to detect the connection of one, or more than one component, of such an extracorporeal blood set.

As can generally be appreciated from FIGS. 2-3, the integrated tubing and filter module (identified by the reference numeral 372) includes the filter 320 and all the tubing and related components described above which are connectable to apparatus 360. For example, the filter and tubing may be retained on a plastic support member 374 which is, in turn, connectable to apparatus 360 (e.g., connectable to the system housing 393 of the apparatus 360). When in the operative position connected to apparatus 360, flexible fluid conducting tubing lines to and from the filtration unit 320 are held in operative, pump communicative loops for operative contact with the peristaltic pumping members of the pumps 324, 344, 346 and 366 to cause the fluid to flow through the primary (blood) and secondary (processing fluid) circuits 312 and 340. Module 372, including filter 320 and all the tubing lines and associated flow components may be disposable after use. The peristaltic pumping members of pumps 324, 344, 346, and 366 may be fixedly disposed on apparatus 360 (without the disposable tubing loop components) and may be re-usable. In general, electrical, mechanical, or electromechanical components are also fixedly disposed in or on apparatus 360 (e.g., connectable to the system housing 393 of the apparatus 360). Examples of such components include the display screen 361 (e.g., a touch-screen), the bubble detector 326, line clamps 331 and connection apparatus for coupling to the transducer side portions of pressure pod apparatus used to implement pressure sensors 327, 328, and 354 as is described herein.

Measurements by the pressure sensors 327, 328 and 354, as well as the return line pressure sensor connected to the deaeration chamber monitor line 391 may be used for one or more various control functions (e.g., used by the apparatus 360 in internal monitoring to make internal decisions and/or automatic adjustments to modify fluid flow parameters). The present disclosure is not limited in the manner the pressure sensor measurements are used by the system in which they are present.

Figure 4:
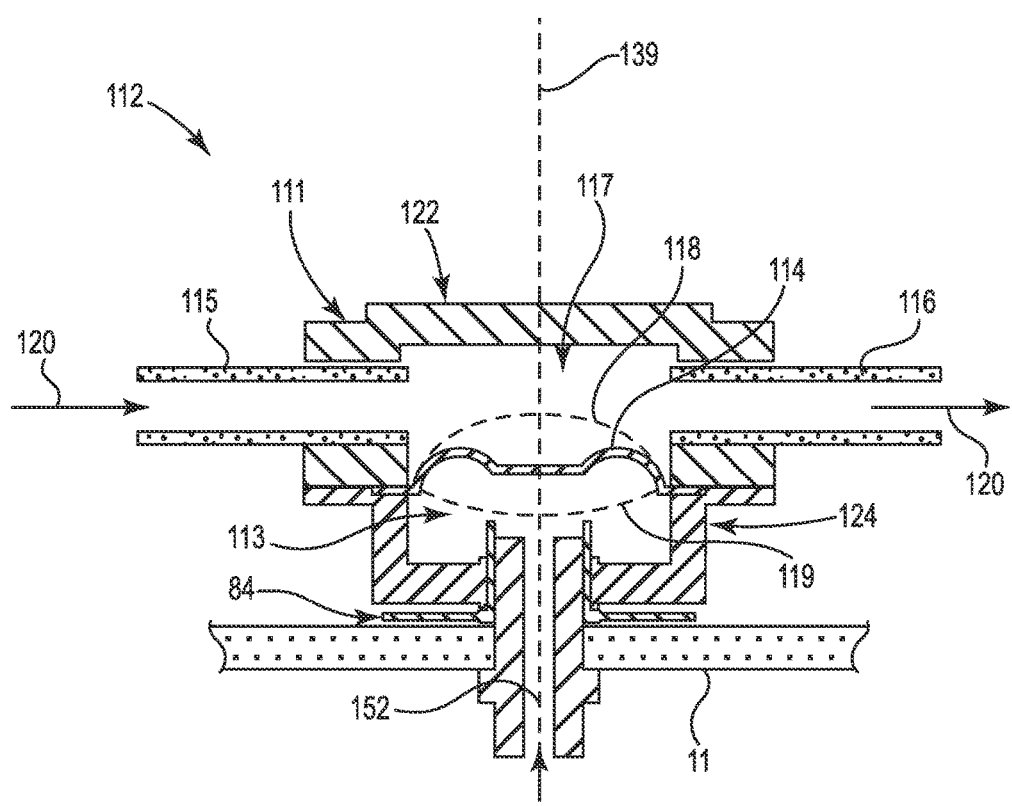
FIG. 4 is a cross-section view of an exemplary pressure pod apparatus mounted on a system housing (e.g., using a connection apparatus) which may be used in a system, for example, such as shown generally in FIGS. 1-3.

One or more of the pressure sensors 327, 328, and 354 may be provided with use of a pressure pod apparatus of a diaphragm type as described herein, for example, with reference to FIGS. 1, 4, and 5A-5C. One or more of the pressure sensors 327, 328, and 354 used may be separated into two distinct portions because the tubing segments 314, 316 and 342, and all other flow components which come into contact with blood and/or blood waste products are, at least in one embodiment, disposable. As such, at least the blood side components of these pressure sensors (e.g., the pressure pod apparatus 112 of each sensor as shown in FIG. 4) are thus also, at least in one embodiment, disposable (e.g., part of extracorporeal blood set 372). The electrical transducers are generally expensive and thus it is desirable that they be incorporated into apparatus 360; and thus, are reusable.

FIG. 4 is an illustrative diagram showing a connection (e.g., detectable according to the present disclosure) of a removable pressure pod apparatus 112 (e.g., equatable to pressure pod apparatus 80A-80C shown in FIG. 1) to system housing 11 (e.g., a system housing that contains one or more pressure transducers, a controller, valves, tubing, etc., such as housing 393 of FIGS. 2-3). Connection apparatus (or point of connection) between the pressure pod apparatus 112 and the system housing 11 (including to the components therein) is shown generally as connection apparatus 84 in FIG. 4 (e.g., such connection apparatus may be similar to that used to mount pressure pod apparatus 412 in mating receptacle 545 of connection apparatus 540 shown in FIGS. 5-6, and such as may be associated with apparatus 360 shown and described with reference to FIGS. 2-3).

In one or more embodiments, the pressure pod apparatus 112 may include a pressure pod body 111 that includes at least a pod body portion 122 and a base body portion 124 (e.g., a pressure pod body that may be coupled in a mating receptacle). As shown in the exemplary embodiment of FIG. 4, a diaphragm 114 (e.g., a flexible membrane) separates the liquid side cavity 117 defined at least in part by the pod body portion 122 from the transducer side cavity 113 (e.g., a close container portion) defined at least in part by the base body portion 124. The liquid side cavity 117 is in fluid communication with an inlet 115 and an outlet 116 (e.g., through which liquid flows as indicated by arrows 120). The diaphragm 114 is displaceable from a centered measuring position (e.g., along axis 139) into the liquid side cavity 117 towards the pod body portion 122 as shown by dashed line 118 and is displaceable from the centered measuring position (e.g., along axis 139) into the transducer side cavity 113 towards the base body portion 124 as shown by dashed line 119. In other words, the flexible diaphragm 114 may flex as generally shown by positions 119 and 118.

As shown in the exemplary embodiment of FIG. 4, when in use, liquid would flow within the extracorporeal circuit between the inlet 115 and the outlet 116 of the pressure pod apparatus 112. The pressure of the liquid in liquid side cavity 117 flexes the diaphragm 114 until the pressure or force on both sides of the diaphragm 114 equalize. The flexible diaphragm 114 expands and contracts based upon the pressure exerted in the liquid side cavity 117 and the mass of gas in the connected tubing and transducer side cavity 113 (e.g., air cavity), atmospheric pressure, and temperature. For example, to measure the pressure exerted by the fluid (e.g., liquid such as blood) in liquid side cavity 117, a pressure transducer is connected via a connection path through a series of tubes/valves to the transducer side cavity 113 (e.g., via a port defining a channel 152 extending through the connection apparatus 84). For example, such connection tubes used for connecting the pressure transducer to the transducer side cavity 113, or other connection tubing described or used herein, may be made from a polymer material suitable for preventing leakage in the pressure range of −700 to 700 mmHg.

In other words, for example, as shown in FIGS. 1 and 4, a pressure sensor with disposable components may include a disposable portion such as the pressure pod apparatus 112 which includes the pressure pod body 111 (e.g., a rigid, plastic casing sometimes referred to as a "pod"). The pressure pod apparatus 112 includes the diaphragm 114 disposed therein separating the pod body 111 into two fluid-tight compartments or cavities 117 and 113. The inlet 115 and the outlet 116 open into cavity 117 to allow liquid to flow into and through the cavity 117 (also referred to herein as the liquid side cavity). The other cavity 113 on the opposing side of the diaphragm 114 has at least one access point (e.g., generally only one access point) to allow for fluid communication therewith (e.g., for communication of a dry gas such as air with the cavity 113 (although wet/wet transducers may also be usable with the pressure pod apparatus 112)). This cavity 113 is also referred to herein as the transducer side cavity or compartment because a transducer is in pressure-sensing communication with the air (e.g., a dry gas) on this transducer side of diaphragm 114. As used herein, air, gas, and dry gas are used interchangeably.

At least in one embodiment, the pressure pod apparatus 112 including the diaphragm 114 is the disposable part of the pressure sensor (e.g., pressure sensor 327, 328, and 354). For example, when the pressure pod apparatus 112 is used with apparatus 360, apparatus 360 may include a corresponding mating receptacle (e.g., as part of a connection apparatus) in and/or to which each disposable pod apparatus 112 is connected (e.g., the mating receptacle being shown generally by the connection apparatus 84A-84C in FIG. 1 provided and/or mounted on system housing 11) putting the transducer side cavity 113 into fluid communication with, for example, a pressure sensing transducer disposed in the apparatus 360. Further, the transducer side cavity 113 may also simultaneously be put in fluid communication with an internal control unit/fluid tubing system.

Liquid flowing through the flow side cavity 117 of such a pressure pod apparatus 112 has an inherent fluid pressure which acts on the diaphragm 114 by moving it. When the diaphragm moves, the diaphragm either compresses or allows expansion of the fluid/dry gas in the transducer side cavity 113 (e.g., on the transducer side of the diaphragm 114). The pressure of the compressed or expanded fluid is sensed by the corresponding pressure transducer inside the control apparatus 360 (e.g., such as pressure transducers P1-P3 shown generally in FIG. 1). The pressure transducer converts the sensed pressure to an electrical signal which is sent to a controller, such as controller 20 shown in FIG. 1 (e.g., an electrical microprocessing unit in control apparatus 360 for analysis of the signals or for interpretation of the signal as a pressure value), which may then process the signal for display, storage or use by software (or hardware) for calculations, or for carrying out any other functionality.

The connection apparatus 84A-84C as shown in FIG. 1, for example, provided as part of the system housing 11 or mounted thereon (e.g., a mating receptacle such as a receptacle mounted on the system housing 393 of the apparatus 360 as shown in FIGS. 2-3), may be of any suitable configuration for use in coupling with the pressure pod apparatus 112 and putting the transducer side cavity 113 into fluid communication with, for example, a pressure sensing transducer (e.g., a pressure sensing transducer disposed in the apparatus 360 coupled by tubing to the connection apparatus). For example, such pressure pod apparatus 112 and mating connection apparatus (e.g., receptacles) may include configurations like those shown in FIGS. 5-6. However, any suitable configuration of the pressure pod apparatus and mating connection apparatus may be used.

At least in one or more embodiments, the connection apparatus 84A-84C includes retention structure for coupling to and retaining one or more portions of the pressure pod apparatus 112 therein (e.g., maintaining the pressure pod apparatus in a stable fixed position, but still being removable from the receptacle). Further, for example, such connection apparatus may provide a port to connect the transducer side cavity 113 to the pressure transducer pressure transducers (e.g., P1-P3 shown generally in FIG. 1) contained in the system housing 11 when the pressure pod body 112 is mounted on the system housing 11 by the connection apparatus 84A-84C.

In other words, the pressure pod apparatus 112 may be of one or more various configurations. For example, the pod body 111 may take any shape as long as a diaphragm 114 separates the liquid side cavity 117 from the transducer side cavity 113 and permits effective transfer of pressure from the liquid flow in liquid side cavity 117 to transducer side cavity 113. For example, in one or more embodiments, the pressure pod body 111 may be formed of one or more components or portions thereof sealed together or may be a unitary structure. For example, the pod body portion 122 may be a separate body component having a surface sealed against a separate base body portion 124 and clamping the diaphragm 114 therebetween. Further, the pressure pod body 111 may be formed of any suitable material such as a polymer (e.g., polyvinyl chloride, polycarbonate, polysulfone, etc.).

Figure 5A:
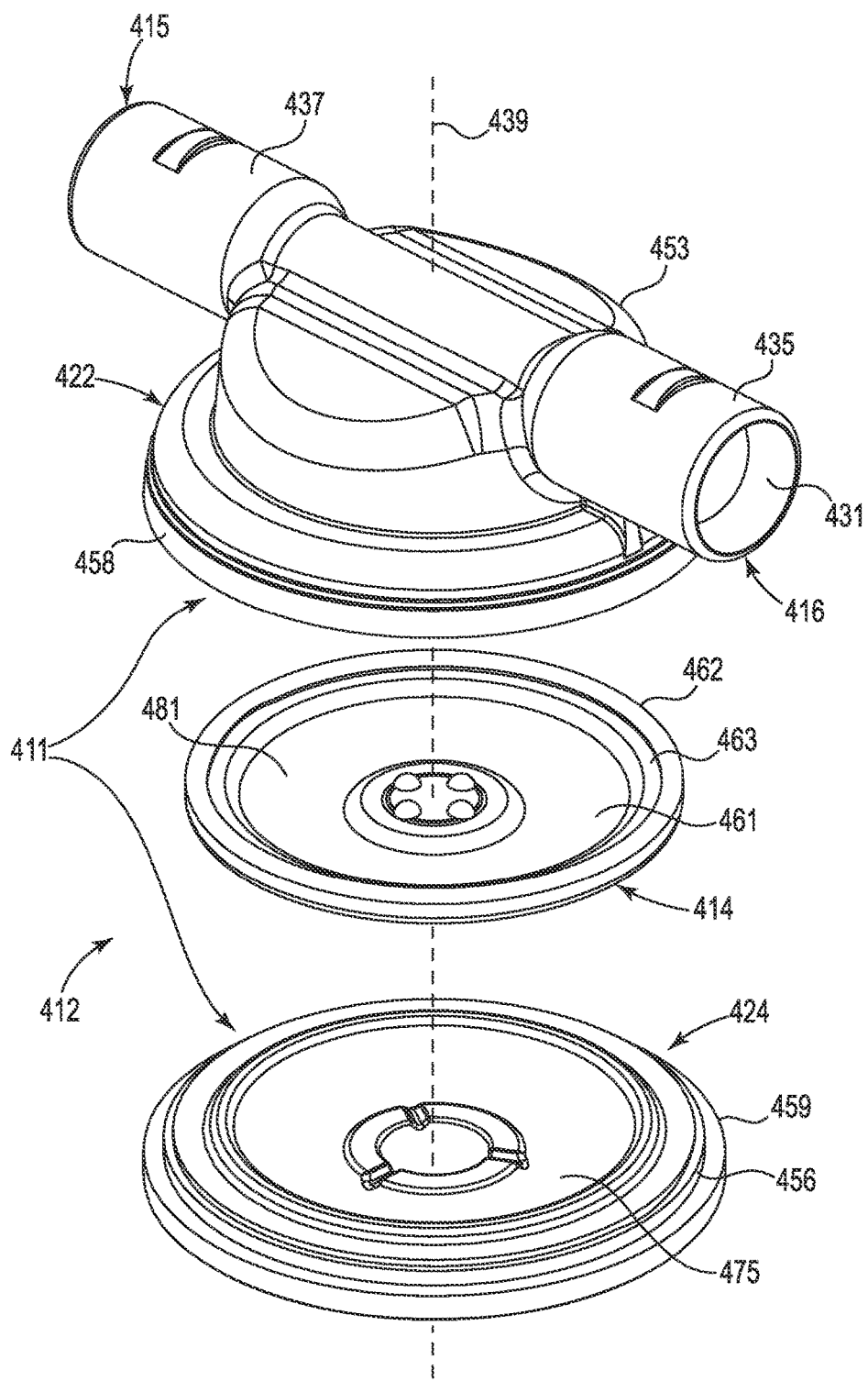
FIGS. 5A-5C show an exploded top perspective view, an exploded bottom perspective view, and a cut-away or cross-section perspective view of an exemplary pressure pod apparatus, such as generally shown in FIG. 4.
Figure 5B:
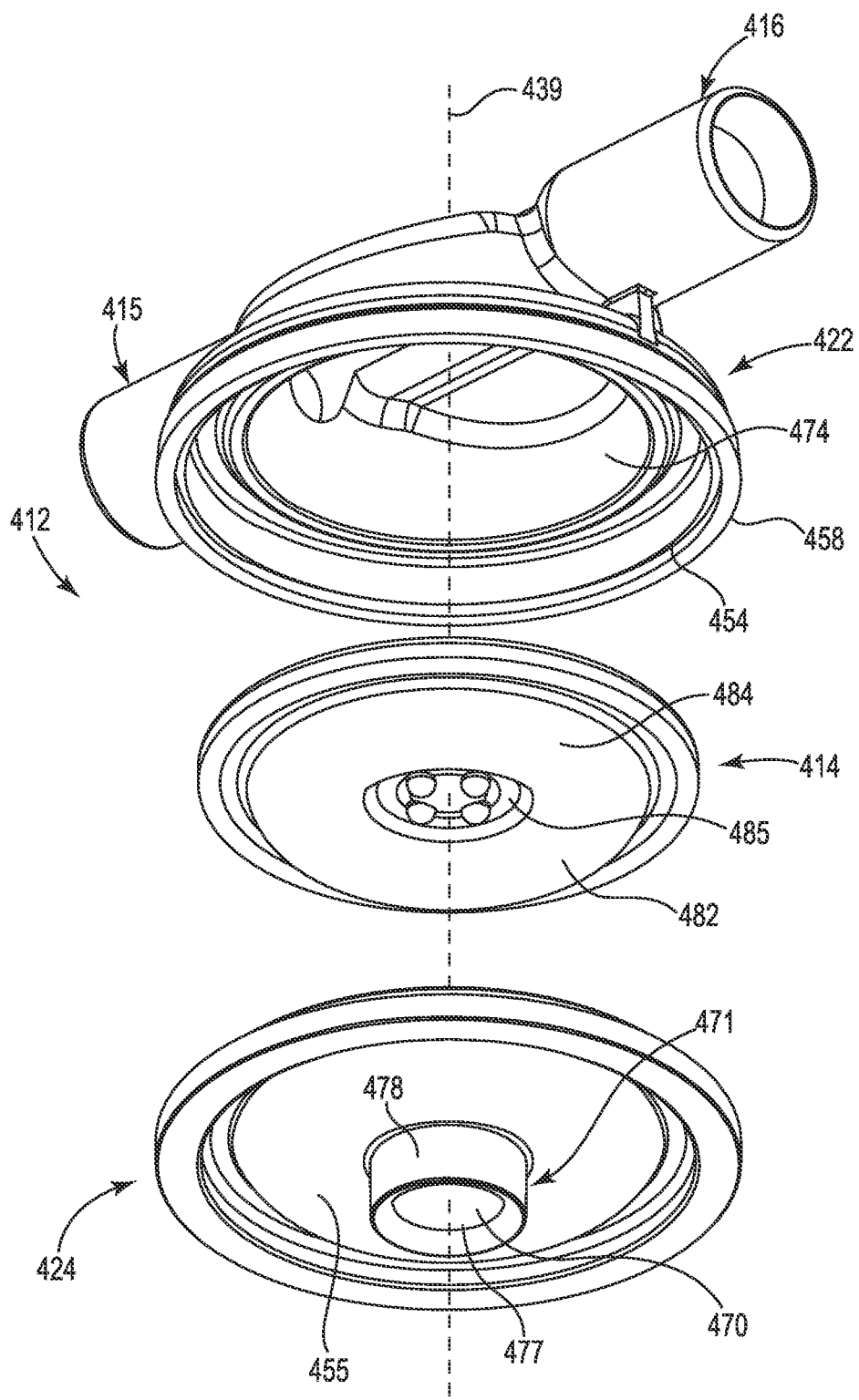
Figure 5C:
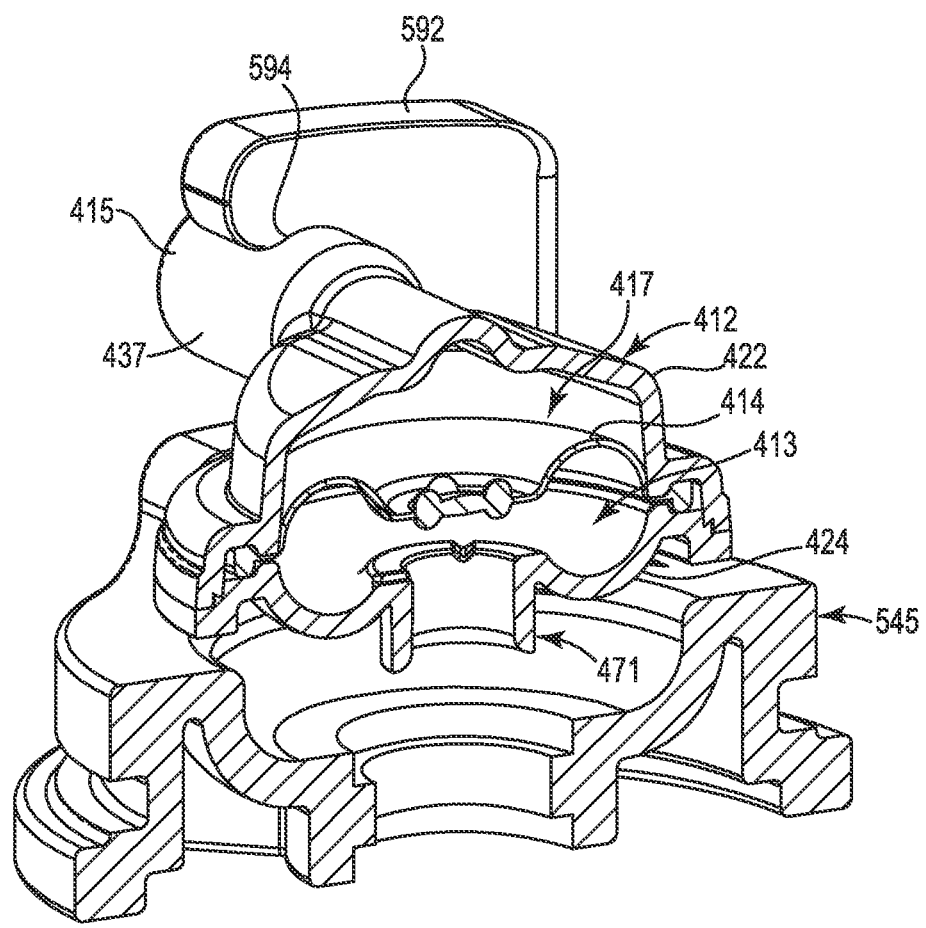

FIGS. 5A-5C show an exploded top perspective view, an exploded bottom perspective view, and an exploded side view of one embodiment of an exemplary pressure pod apparatus 412. The pressure pod apparatus 412 includes a pressure pod body 411 including at least a pod body portion 422 and a base body portion 424. For example, the pod body portion 422 which defines at least a portion of the liquid side cavity 417 (see, FIG. 5C) may include an annular clamping portion 454 extending from an annular edge 458 inward towards axis 439. A generally concave portion 453 (e.g., which includes an inner surface 474 adjacent the liquid side cavity 417) is located inward of the annular clamping region 454 relative to axis 439. The generally concave portion 453 or dome section terminating the annular clamping region 454 along axis 439 (e.g., a generally concave portion facing the base body portion 424 and lying along the axis 439 with its center on the axis 439) includes an inlet 415 and an outlet 416 extending from the pod body portion 422 (e.g., from the generally concave portion 453) to allow, for example, connection of tubing thereto, and to provide a path for liquid to enter and exit the liquid side cavity 417. For example, each of the inlet 415 and outlet 416 includes a cylindrical element 435 defining an inner surface 431 for mating with a tube. The cylindrical element 435 also includes an outer surface 437 configured for mating with connection apparatus (e.g., such as to mate with retention structure of a receptacle such as that shown in FIGS. 6A-6C).

The base body portion 424, for example, which defines at least a portion of the transducer side cavity 413, may include an annular clamping portion 456 extending from an annular edge 459 inward towards axis 439. A generally concave portion 455 (e.g., which includes an inner surface 475 adjacent the transducer cavity 413) is located inward of the annular clamping region 456 relative to axis 439. The generally concave portion 455 or dome section terminating the annular clamping region 456 along axis 439 (e.g., a generally concave portion facing the pod body portion 422 and lying along the axis 439 with its center on the axis 439) includes a cylindrical port 471 including an access opening 470 (e.g., defined through the generally concave portion 455) to allow, for example, fluid communication between the transducer side cavity 413 and a pressure transducer provided as part of the fluid processing system (e.g., as part of the control apparatus 360 shown in FIGS. 2-3). For example, the port 471 may include an inner surface 477 which may receive a portion of a connection apparatus (e.g., such as to mate with a receptacle such as that shown in FIGS. 6A-6C). Further, for example, the port 471 may include an outer surface 478 which may mate with a portion of a connection apparatus (e.g., such as to mate with a receptacle such as that shown in FIGS. 6A-6C). Further, the mating between the port 471 and the connection apparatus may provide a seal therebetween (e.g., such that transducer side cavity 413 is a fluid tight cavity (e.g., when taking into consideration the other pressure sensing components such as tubing, pumps, etc.). Such a seal may be provided in any suitable manner, such as with use of a sealing device (e.g., an o-ring, sealing material, etc.).

The pressure pod apparatus 412 further includes diaphragm 414. For example, the diaphragm 414 includes an annular clamp region 463 extending from an annular edge 462 inward towards axis 439. A deflection portion 461 (e.g., which includes a first surface 482 adjacent the transducer side cavity 413 and a second surface 481 adjacent the liquid side cavity 417) is located inward of the annular clamp region 463 relative to axis 439. The deflection portion 461 may include a bias such that it includes one or more regions which extend further in the transducer side cavity 413 than other regions thereof, or a bias such that it includes one or more regions which extend further into the liquid side cavity 417 than other regions, which may be referred to as a diaphragm bulge (e.g., an annular region 484 of the deflection portion 461 extends into the transducer side cavity further than a center region 485 at axis 439 as shown in FIG. 5B, or for other configurations this may be reversed). Depending on whether the pressure to be measured is positive or negative, the diaphragm bulge may be placed in a particular direction giving a larger range in the pressure range of interest (e.g., either positive or negative). The annular clamp region 463, when the pressure pod apparatus 412 is assembled, is clamped between annular clamping region 456 of the base body portion 424 and the annular clamping region 454 of the pod body portion 422 to form the cavities 413 and 417 on either sides of the diaphragm 414. Any suitable processes and materials may be used to provide such an assembly (e.g., adhesives, thermal processing, etc.).

Figure 6A:
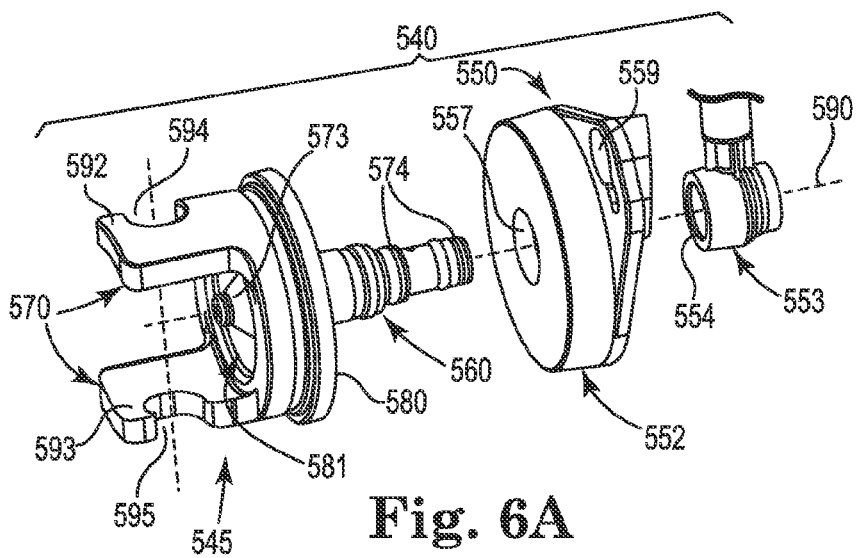
FIGS. 6A-6B show an exploded perspective view and a bottom view of a connection apparatus to connect a pressure pod apparatus, such as shown in FIGS. 5A-5C, to a fluid processing system (e.g., mount the pressure pod apparatus on a system housing).
Figure 6B:
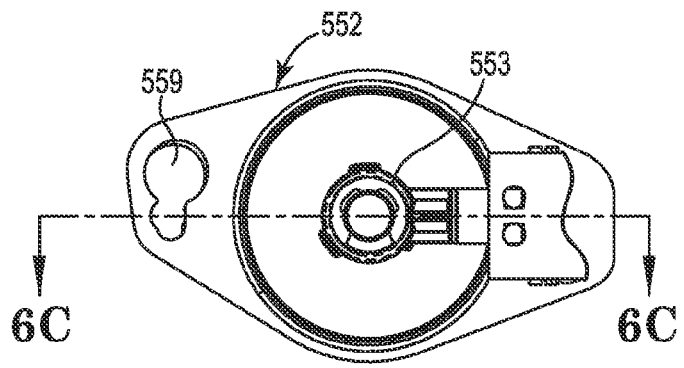
Figure 6C:
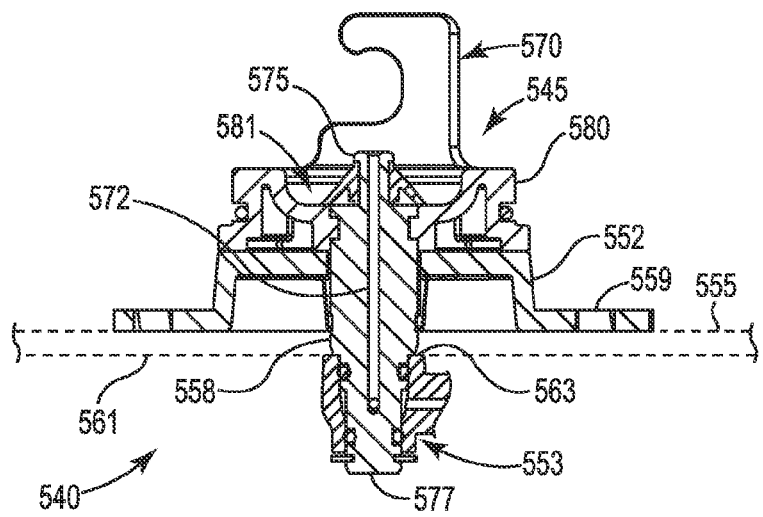
FIG. 6C is a cross-section of the connection apparatus shown in FIG. 6B taken at line C-C.

FIGS. 6A-6B show an exploded perspective view and a bottom view of a connection apparatus 540 mountable on a system housing (e.g., such as system housing 11 shown in FIG. 1 or system housing 393 of FIGS. 2-3) to connect a pressure pod apparatus (e.g., provided as part of a disposable extracorporeal blood set), such as pod apparatus 412 shown in FIGS. 5A-5C, to a fluid processing system (e.g., such as fluid processing system 360 shown in FIGS. 2-3). FIG. 6C is a cross-section of the connection apparatus 540 shown in FIG. 6B taken at line C-C.

For example, the connection apparatus 540 may include a receptacle 545 configured to mate with a pressure pod apparatus (e.g., retain pressure pod apparatus 412 therein in a particular fixed position), and mounting apparatus 550 for mounting the mating receptacle 545 with respect to a system housing (see dashed system housing 555 in FIG. 6C). For example, mounting apparatus 550 may include an internal mounting structure 552 for receiving at least a portion of the mating receptacle 545 (e.g., port 560) in an opening 557 defined therein aligned with an opening defined in system housing 555. Further, the mounting apparatus 550 may include an internal connection structure 553 (e.g., tubing and tubing connectors that mate with a portion of the mating receptacle 545 (e.g., port 560) when inserted through the opening 557 of the internal mounting structure 552 to allow for fluid communication from inside of the system housing 555 to the transducer side cavity 417 of the pressure pod apparatus 412. The mounting of the mating receptacle 545 to the housing may be implemented with use of at least one of the internal mounting structure 552 being mounted to the system housing 555 (e.g., via one or more fasteners using openings 559), the internal connection structure 553, interference fit between a part of the mating receptacle 545 with the internal mounting structure 552 (e.g., an interference fit between a portion of the port 560 within the opening 557 defined in the internal mounting structure 552), or in any other suitable manner to provide a fixed mating receptacle 540 on the system housing 555 and/or relative thereto. Further, for example, an o-ring 558 or other suitable sealing device may be used to prevent liquid ingress into the interior of the system housing 555.

The mating receptacle 545 may include an annular body portion 580 extending along axis 590 defining a receiving region 581 to receiving a portion of the pressure pod apparatus 412 (e.g., to receive at least a part of the pod body portion 424 thereof). The port 560 (e.g., an elongate structure providing a fluid channel 572 therethrough) may extend along axis 590 through the annular body portion 580 from a first end region 575 to a second end region 577. The first end region 575 is configured for coupling with the port 471 of the pressure pod apparatus 412 (e.g., mate with the inner surface 477 thereof). For example, the mating between the port 471 and the first end region 575 of the port 560 may provide a seal therebetween (e.g., such that transducer side cavity 413 is a fluid tight cavity (e.g., when taking into consideration the other pressure sensing components such as tubing, pumps, etc.). For example, one or more lip seals 573 may be provided at the first end region 575 to sealingly mate with the inner surface 477 of the port 471 of the pressure pod apparatus 412. However, such seal to provide a fluid tight connection may be provided in any suitable manner, such as with use of any sealing apparatus on any of the components (e.g., an o-ring, sealing material, etc.).

The second end region 577 is configured for coupling with the internal connection apparatus 553 (e.g., mate with an inner surface 554). For example, the mating between the internal connection apparatus 553 and the second end region 577 of the port 560 may provide a seal therebetween (e.g., such that transducer side of the pressure sensor components provide fluid tight communication between the transducer side cavity 413 of the pressure pod apparatus 412 and a pressure transducer contained with the system housing 555. For example, one or more o-ring seals 574 may be provided at the second end region 577 to sealingly mate with the inner surface 554 of the internal connection apparatus 553. However, such a seal to provide the fluid tight connection may be provided in any suitable manner, such as with use of any sealing apparatus on any of the components (e.g., an o-ring, sealing material, etc.).

The mating receptacle 545 also may include retention structure 570 for coupling to and retaining one or more portions of the pressure pod apparatus 412 therein (e.g., maintaining the pressure pod apparatus in a stable fixed position). For example, as shown in FIGS. 6A and 6C, the retaining structure 570 may include U-shaped elements 592 and 593 positioned relative to and/or extending from the annular body portion 580 at a distance from axis 590. Such U-shaped elements 592-593 define channel openings 594-595 that are open in opposing directions and which lie along an axis 591 (e.g., an axis 591 that is orthogonal to axis 590). The channel openings 594-595 are configured to receive a portion of each of the inlet 415 and outlet 416 (e.g., which also lie along an axis), respectively (e.g., receive the outer surface 437 of each cylindrical element 435 configured for mating within the respective channel openings 594-595 of retention structure 570 (e.g., upon aligning the axis 439 of the pressure pod apparatus 412 with the axis 590 of the receptacle 545 and pushing and/or turning the pressure pod apparatus 412 about the axis 590 such that the outer surface 437 of each cylindrical element 435 is mated within the respective channel openings 594-595 of retention structure 570). However, any suitable mating configurations that provide for stable positioning of the pressure pod apparatus 412 on the system housing may be used and the present disclosure is not limited by only the mating configurations described herein.

Figure 7:
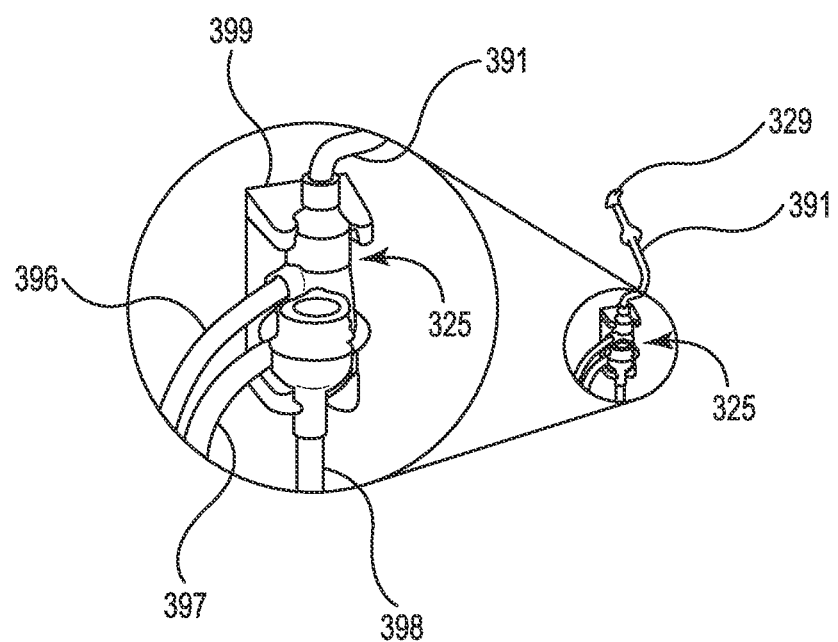
FIG. 7 is a perspective view of an exemplary deaeration chamber mounted on a system housing, wherein a deaeration chamber monitor line connects the deaeration chamber to a pressure transducer within a system housing of a system, for example, such as shown generally in FIGS. 1-3, to monitor return line pressure.

FIG. 7 shows the deaeration chamber 325 of FIGS. 2-3 positionable in a chamber holder 399 and connectable in the return line. As shown, a deaeration chamber monitor line 391 (e.g., generalized as open line element 82 in FIG. 1) connects the deaeration chamber 325 to an internal pressure transducer within the system housing 393 (e.g., generalized as pressure transducer Pline in FIG. 1) using a connection apparatus, such as, for example, a return pressure port 329 (e.g., generalized as port 86 in FIG. 1). This enables return pressure monitoring of the blood in the return line provided as an input to the deaeration chamber 325 via input line 397 and output therefrom via output line 398. Replacement fluid may be provided via line 396 on top of the blood to prevent an air/blood interface.

The connection apparatus 86 (e.g., return pressure port 329) for providing connection of the open line element 82 (e.g., deaeration chamber monitor line 391) may be any suitable port allowing a user to connect the open line element 82 thereto and provide a sealed connection such that valid pressures may be sensed by the transducer (e.g., Pline) within the system housing 11 (e.g., system housing 393). For example, such connection apparatus may include luer fittings and connectors, fluid barriers, or any other like fluid connection apparatus.

With further reference to FIG. 1, which is illustrative of an extracorporeal fluid system such as shown and described with reference to FIGS. 2-3, each of the plurality of removable pressure pod apparatus 80A-80C (e.g., such as pressure pod apparatus 412 shown in FIGS. 5A-5C) which may be part of an extracorporeal blood set 22 are removably connectable to the system housing 11 (e.g., a system housing that contains one or more pressure transducers, a controller, valves, tubing, etc.) using connection apparatus 84A-84C (e.g., such connection apparatus may be similar to that used to mount pressure pod apparatus 412 in mating receptacle 545 of connection apparatus 540 shown in FIGS. 5-6).

The system 10 further includes the pump apparatus 14 which may be used to automatically reposition the diaphragm (e.g., diaphragm 114) of pressure pod apparatus 80A-80C towards the centered measuring position. For example, such repositioning may be implemented using pump apparatus 14 in a controlled system (e.g., feedback system). For example, air may be infused or extracted using pump apparatus 14 (e.g., an air pump connected to the transducer side cavity of the pressure pod apparatus) through one or more valves 88A-88C (e.g., 2 port/2 way solenoid valves) controlled by one or more corresponding switches S1-S3. As such, the pump apparatus 14 may sometimes be referred to herein as the automatic repositioning system (ARDS) air pump. In at least one embodiment, the air pump apparatus 14 may include a peristaltic pump which may be driven clockwise to infuse air into the system (e.g., in the air or transducer side cavity of a pressure pod) or may be driven counter-clockwise to remove air therefrom.

Likewise, the open line element 82 (e.g., such as deaeration chamber monitor line 391 shown in FIG. 7) which may be part of an extracorporeal blood set 22 are removably connectable to the system housing 11 using connection apparatus 86 (e.g., a return pressure port 329 as shown in FIG. 7). The pump apparatus 14 may be used to infuse air into or extract air from the open line element 82 through valve 90 (e.g., 2 port/2 way solenoid valves) controlled by corresponding switch Sline. It will be recognized by one skilled the art that the number of pressure pod apparatus (or other components including closed container portions), or the number of open line elements is not limited, and the present disclosure contemplates implementation of component connection detection with respect to any number of components.

As shown in the embodiment of FIG. 1, the controller 20 (e.g., within the system housing 11) is operatively coupled to receive one or more signals (e.g., representative of the pressures as sensed by pressure transducers, such as Pline, Ppump, P1-P3, etc.) and generate control signals for use in controlling pump apparatus 14. The pump apparatus 14 and valves 88A-88C, 90 via switches S1-S3, Sline may be controlled to provide air to the connection points of the various components. For example, the controller 20 may be configured to operate a different valve (e.g., of valves 88A-88C, 90) for each component to be connected to the system 10 to allow air from the air pump apparatus 14 to be provided for use in detecting whether each respective component to be connected has been properly connected. In other words, the plurality of valves 88A-88C, 90 allow a single pump apparatus to be used for detecting the connection of multiple components. Further, for example, using the various pressure signals (e.g., including pressures associated with port 86 and sensed using pressure transducer Pline, pressures associated with pressure pod apparatus 80A-80C and sensed using pressure transducers P1-P3, as well as pressures between pump apparatus 14 and valves 88A-88C, 90 sensed by pressure transducer Ppump), controller 20 may be used to determine whether one or more of the components (e.g., pods 80A-80C, open line element 82, etc.) are operatively connected such that valid pressure measurements may be obtained during treatment procedures.

The controller 20 may be any hardware/software architecture configured to provide the desired functionality. For example, the controller may include circuitry for sampling pressure measurements from the transducers, processing apparatus and associated software for processing data (e.g., signals representative of the pressures), output circuitry to generate control signals for use in component connection detection or presenting information on the graphical user interface (e.g., switch signals, air pump control or drive signals, etc.). As described herein with reference to FIGS. 2-3, for example, such controller functionality may be carried out by the apparatus 360 described therein.

Such processing apparatus, may be, for example, any fixed or mobile computer system (e.g., a personal computer or mini-computer associated with, for example, a fluid treatment or processing system, such as a dialysis system). The exact configuration of the computing apparatus is not limiting and essentially any device capable of providing suitable computing capabilities and control capabilities (e.g., perform component connection detection, provide a graphical user interface, for example, to provide instructions to a user, etc.) may be used. Further, various peripheral devices, such as a computer display, mouse, keyboard, memory, printer, scanner, are contemplated to be used in combination with processing apparatus, and its associated data storage. For example, data storage may allow for access to processing programs or routines and one or more other types of data that may be employed to carry out the illustrative methods and functionality as described herein.

In one or more embodiments, the methods or systems described herein may be implemented using one or more computer programs or processes (or systems including such processes or programs) executed on programmable computers, such as computers that include, for example, processing capabilities, data storage (e.g., volatile or non-volatile memory and/or storage elements), input devices, and output devices. For example, the systems and methods described herein may be considered to include multiple processes or programs that may be implemented alone or in combination. Program code and/or logic described herein may be applied to input data to perform functionality described herein and generate desired output information. The output information may be applied as input to one or more other devices and/or processes as described herein or as would be applied in a known fashion. For example, processing programs or routines may include programs or routines for performing various algorithms, including standardization algorithms, comparison algorithms, or any other processing required to implement one or more embodiments described herein, such as those for performing averaging of measurement data, generation of control signals, etc.

Software or programs used to implement the functionality described herein may be provided using any programmable language, e.g., a high level procedural and/or object orientated programming language that is suitable for communicating with a processing apparatus. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the methods and systems described herein may be implemented using a computer readable storage medium, configured with a computer program, where the storage medium so configured causes the processing apparatus to operate in a predefined manner to perform functions described herein.

Pump apparatus 14 may be connected in the system using any suitable configuration (e.g., a configuration formed of one or more pumps, valves, and tubes) to accomplish the functionality described herein. Pressure transducers (e.g., Pline and P1-P3) may be any suitable transducers and may be operatively configured with respect to the component connection points (e.g., a configuration in the form of valves and tubes) to accomplish the function of sensing pressures at such connection points.

Further, as shown in FIG. 1, an air filter 16 may be provided and connected between the air pump apparatus 14 and the one or more ports associated with the various components (e.g., pressure pod apparatus 80A-80C, monitor line 82, etc.). Such an air filter may be a clarifier air filter when connecting sterile components to such ports. In other words, the clarifying air filter provides clarifying air to maintain the sterile components connected at such ports. For example, such an air filter may include filters such as submicron filters, membrane filters, absorption filters, particulate filters, etc.

In one or more embodiments described herein, the component detection algorithm provides an automated sequence to monitor and detect the correct installation of each pressure pod apparatus, as well as, for example, the return pressure deaeration chamber monitor line. For example, the algorithm may use the automatic repositioning system air pump to inject air into the transducer side air cavity of the pressure pod apparatus or the return monitor line of the deaeration chamber and monitor the results in pressure change in the air cavity or line. Further, for example, electronically controlled valves may be used to control which pressure pod apparatus is connected to the automatic repositioning system air pump output line. If no pressure pod apparatus is installed, no pressure rise will result from the pump action. If a pressure pod apparatus is installed properly (i.e., such that an airtight seal between the pressure pod apparatus and the pod housing or receptacle is created), then a pressure rise will result. In the case of the deaeration chamber monitor line, for example, pressurized air may be released into the return pressure sensor port where the monitor line is to be connected and the resulting pressure spike may be monitored to determine if the monitor line is attached properly. The component connection detection algorithm inputs are used to specify which pressure pod apparatus or monitor line installation is to be verified (e.g., inputs to the controller), and, for example, the order of verification. Further, for example, the component connection detection algorithm may set discretes in the system indicating which pressure pod apparatus or monitor line installations have been completed properly.

For example, in one or more embodiments, no user confirmation that a component has been attached is required. In other words, user confirmation (e.g., using a graphical user interface or in any other manner) that the pressure pod apparatus are connected to the pressure sensor housing (e.g., a sensor receptacle on the system housing) may be unnecessary, thus reducing user workload. For example, in one or more embodiments, the algorithm provides independent verification that the pressure pod apparatus and/or monitor line have been installed correctly by the user, thus eliminating the possibility that the user may incorrectly confirm completion of the connection task. If, for example, the user fails to install the pressure pod apparatus or does not achieve an airtight connection between the pressure pod apparatus and the system housing, the algorithm may "time-out" and set a "pod detection failure" flag which may need to be resolved before continuing machine set up. As such, the risk of erroneous pressure sensor readings from pressure pod apparatus that is not installed or is incorrectly installed is substantially reduced. In addition, such automatic component connection detection of the monitor line to the return pressure port reduces the risk of incorrect operation and potential damage to the disposable set or the components of the system due to an unconnected return pressure monitor line. Further, for example, the component connection detection algorithm may also speed up device set up by eliminating the need for the user to manually confirm the monitor line connection, using, for example, a graphical user interface.

With reference to FIGS. 8-16, one or more embodiments of various component connection detection methods shall be described. For example, one or more embodiments of such methods shall incorporate description of component connection detection in conjunction with a graphical user interface (e.g., a touchscreen, such as, display 361 shown in FIG. 2-3). The methods shall primarily be described with reference to elements of FIG. 1, however, it will be apparent that any fluid handling systems may be used to implement such methods.

Figure 8:
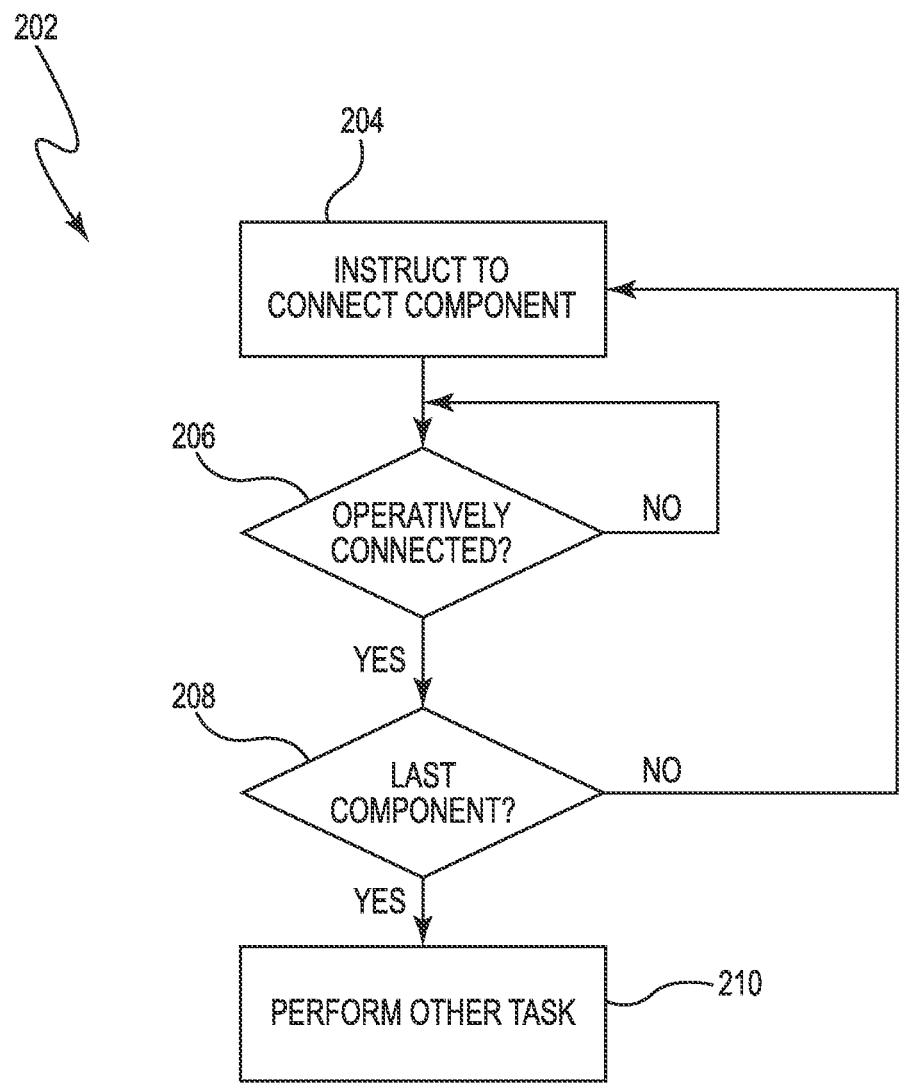
FIG. 8 shows a flow diagram of an exemplary method of connecting one or more components of an extracorporeal blood set to a system housing of a system, for example, such as shown generally in FIGS. 1-3.

For example, the flow diagram of FIG. 8 shows an exemplary component connection detection method 202 for connecting one or more components (e.g., pressure pod apparatus 80A-80C, return monitor line 82, etc.) of an extracorporeal blood set 22 to a housing 11 of an extracorporeal blood treatment system 10. For example, the system housing 11 contains one or more pressure transducers (e.g., Pline, P1-P3, and Ppump) and an air pump apparatus 14 (e.g., an automatic repositioning air pump). Further, the system 10 may include connection apparatus 84A-84C including one or more ports suitable to connect the one or more pressure transducers (e.g., Pline, P1-P3, and Ppump) to the one or more components (e.g., pressure pod apparatus 80A-80C, return monitor line 82, etc.) of the extracorporeal blood set 22.

Figure 16A:
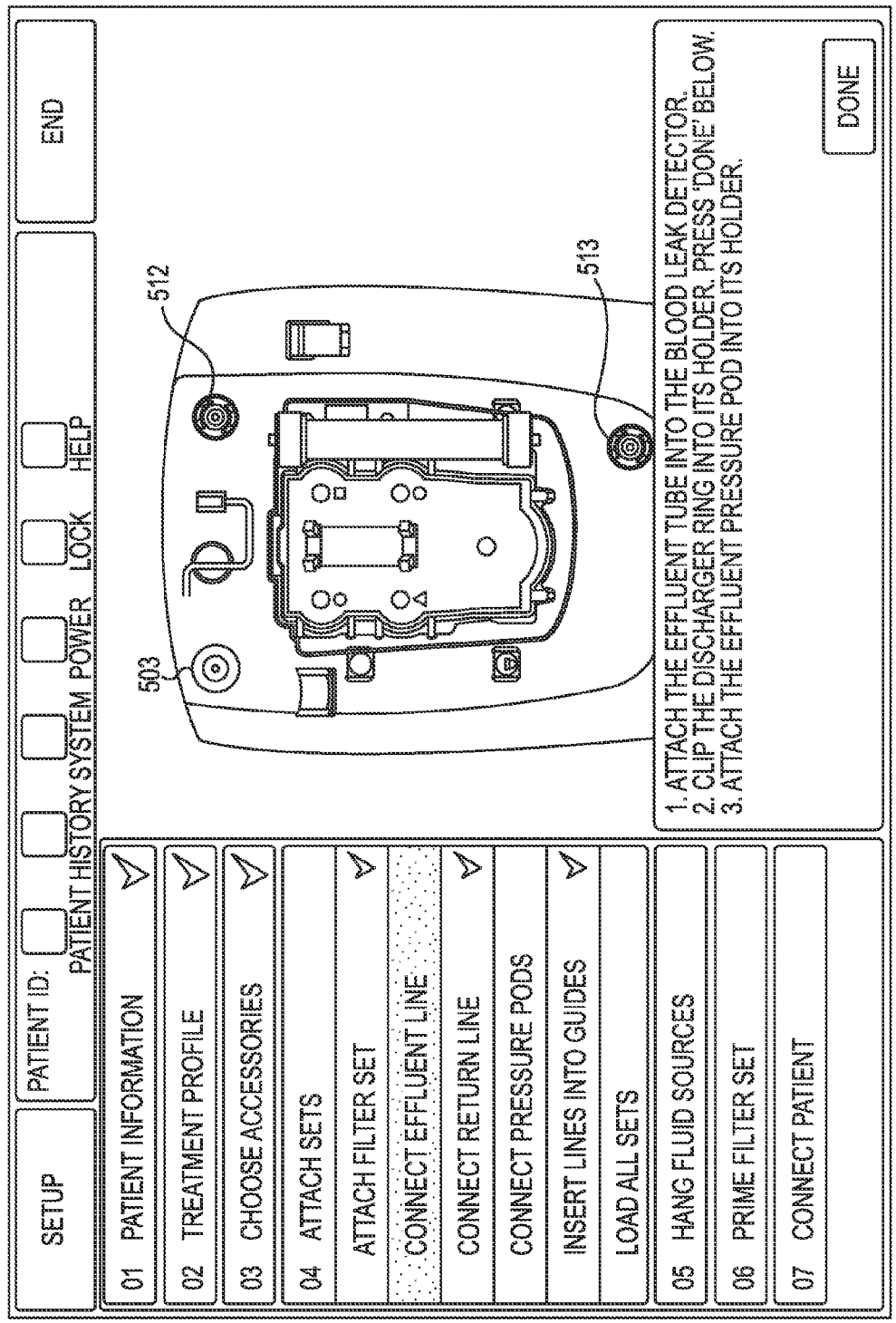
FIGS. 16A-16D show screen shots for use in describing connection of various components to a system housing of a system, for example, such as shown generally in FIGS. 1-3.
Figure 16B:
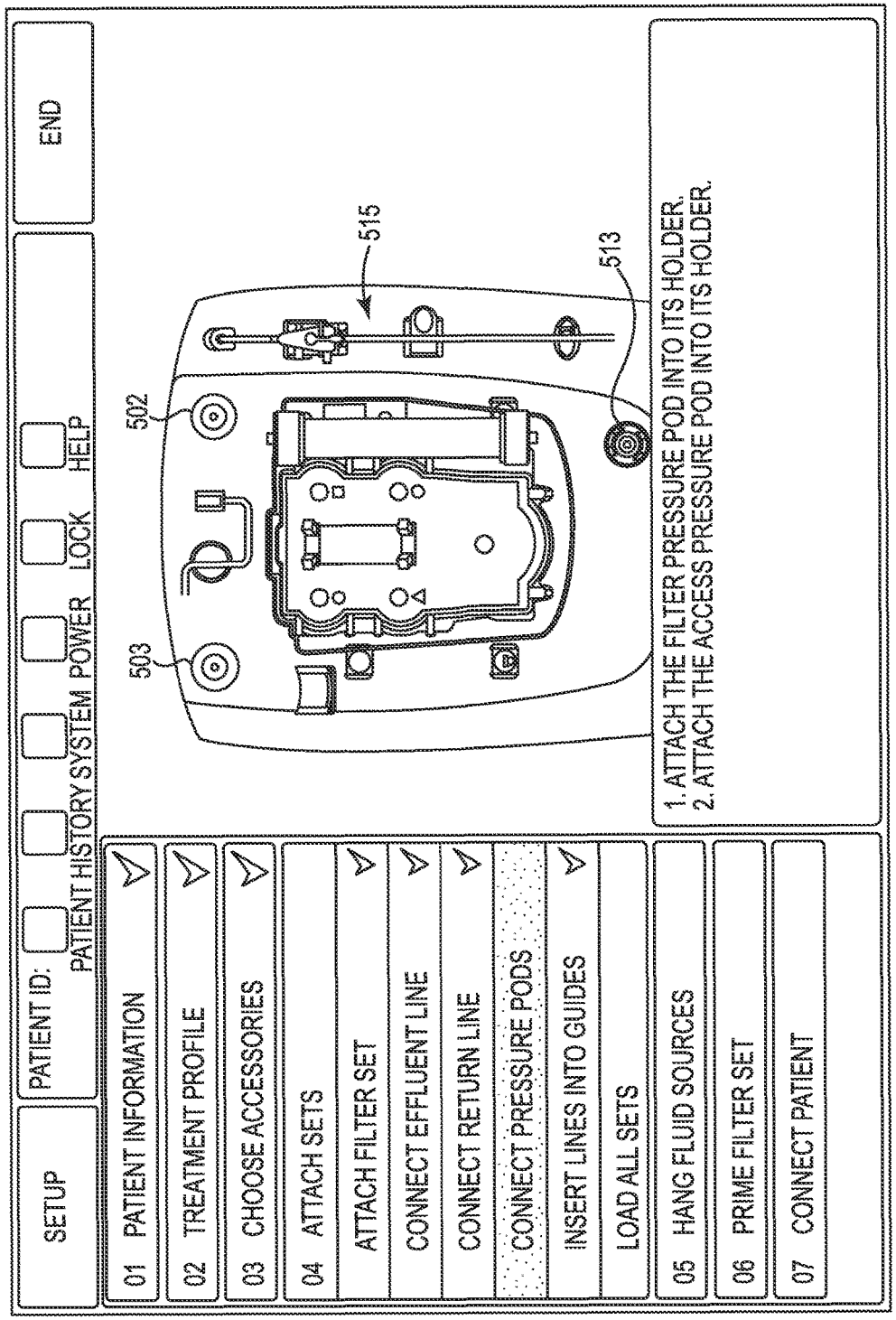

The detection method 202 may include initially instructing a user to connect at least a first component of the one or more components (e.g., pressure pod apparatus 80A-80C, return monitor line 82, etc.) configured to be mounted on the system housing 11 of the extracorporeal blood treatment system 10 (e.g., using mating receptacles, ports, etc.) (block 204). For example, a user may be instructed, via a graphical user interface, to connect a first component (e.g., a pressure pod apparatus, a return monitor line, etc.) to the system 10. For example, as shown in FIG. 16A, during connection of the effluent line (e.g., "Connect Effluent Line" being highlighted in FIG. 16A), the user may be instructed to "3. Attach the Effluent Pressure Pod into its holder." If the system 10 determines that the component is operatively connected (block 206), it may further be determined whether it is the last component to be connected (block 208). If it is the last component to be connected, then the system may instruct the user to perform any other task desired (block 210) (e.g., connect a return line, load all sets, etc.). However, if it is not the last component to be connected (block 208), then the user is instructed to connect one or more other components (i.e., the process may be repeated). For example, although not shown in FIGS. 16A-16D, the user may be instructed when the "Connect Return Line" instruction is highlighted on a graphical user interface to place the deaeration chamber in its holder and attach the deaeration chamber monitor line to the return pressure port. Still further, for example, as shown in FIG. 16B (e.g., "Connect Pressure Pods" being highlighted in FIG. 16B), the user may be instructed to "1. Attach the Filter Pressure Pod into its holder" and, thereafter upon detection of the connection of the filter pressure pod, "2. Attach the Access Pressure Pod into its holder."

Instructions provided after it has been determined that a component (e.g., pressure pod apparatus 80A-80C, return monitor line 82, etc.) has been properly connected, at least in one embodiment, are provided automatically and without intervention by a user. For example, the user is not required to confirm that the user has attached the component. Rather, the user just continues to follow the instructions automatically provided via the graphical user interface. For example, such instructions may be to perform the attachment of another component and/or perform some other task.

In one or more embodiments, to determine whether the component (e.g., pressure pod apparatus 80A-80C, return monitor line 82, etc.) is operatively connected (block 206), air generated by the air pump apparatus 14 is provided to at least one of the one or more ports of the connection apparatus (e.g., connection apparatus 84A-84C, 86) such that a pressure associated with the component is measurable using at least one of the one or more pressure transducers (e.g., pressure transducers Pline and P1-P3). As described herein, the process for determining whether a component that includes a closed container portion (e.g., pressure pod apparatus 80A-80C) is connected properly may be different than the process for determining whether an open line element (e.g., return monitor line 82) is connected properly.

Figure 9:
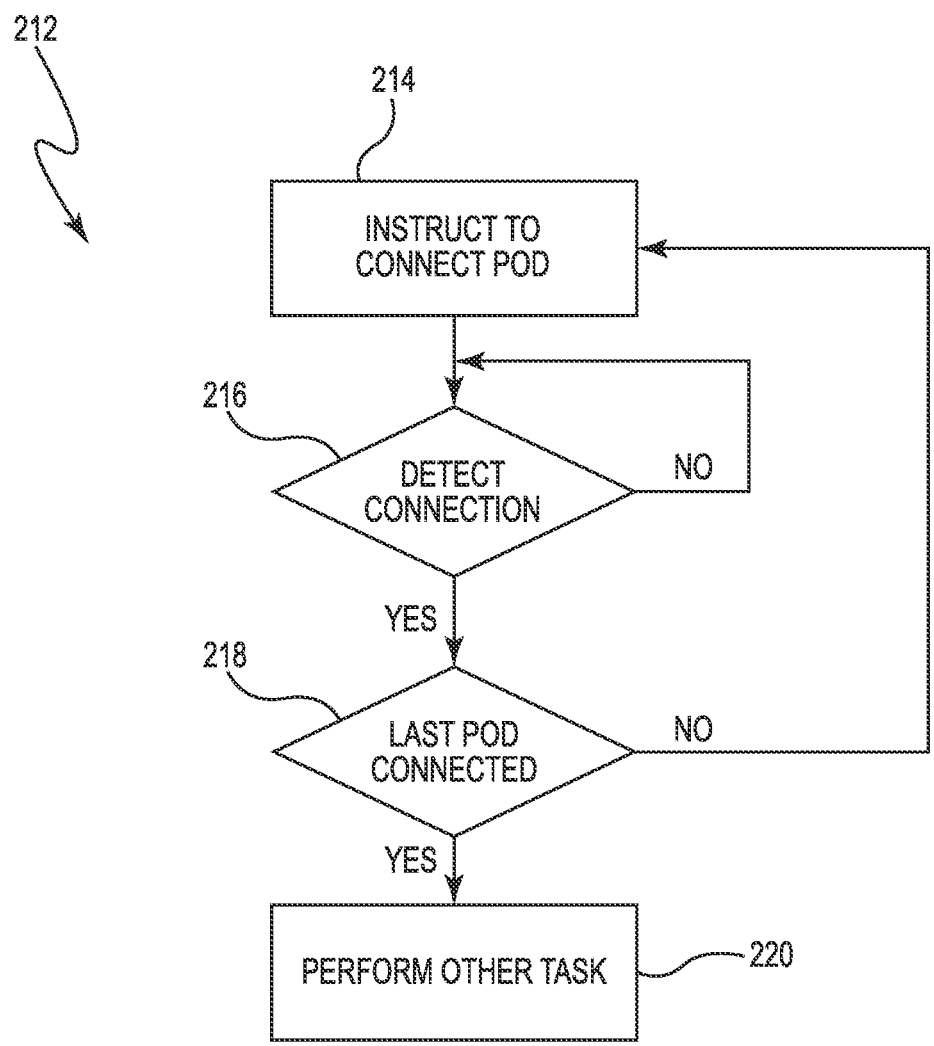
FIG. 9 shows a flow diagram of an exemplary method of connecting pressure pod apparatus of an extracorporeal blood set (which includes a closed container portion) to a system housing of a system, for example, such as shown generally in FIGS. 1-3.

FIG. 9 shows an exemplary component connection detection method 212 for connecting one or more components including a closed container portion (e.g., pressure pod apparatus 80A-80C) to a housing 11 of an extracorporeal blood treatment system 10. For example, the detection method 212 may include instructing a user, e.g., via a graphical user interface, to connect at least a first pressure pod apparatus (e.g., pressure pod apparatus 80A-80C) configured to be mounted on the system housing 11 of the extracorporeal blood treatment system 10 (e.g., using mating receptacles) (block 214). For example, as shown in FIG. 16B, the user may be instructed to "1. Attach the Filter Pressure Pod into its holder." If the system 10 determines that the pressure pod apparatus is operatively connected (block 216), it may further be determined whether it is the last pressure pod apparatus to be connected (block 218). If it is the last pressure pod apparatus to be connected, then the system may instruct the user to perform any other task desired (block 220) (e.g., connect a return line, load all sets as shown in FIG. 16D, etc.). However, if it is not the last pressure pod apparatus to be connected (block 218), then the user may be instructed to connect one or more other pressure pod apparatus (i.e., the process may be repeated). For example, as shown in FIG. 16B, the user may be instructed to "2. Attach the Access Pressure Pod into its holder."

Figure 16C:
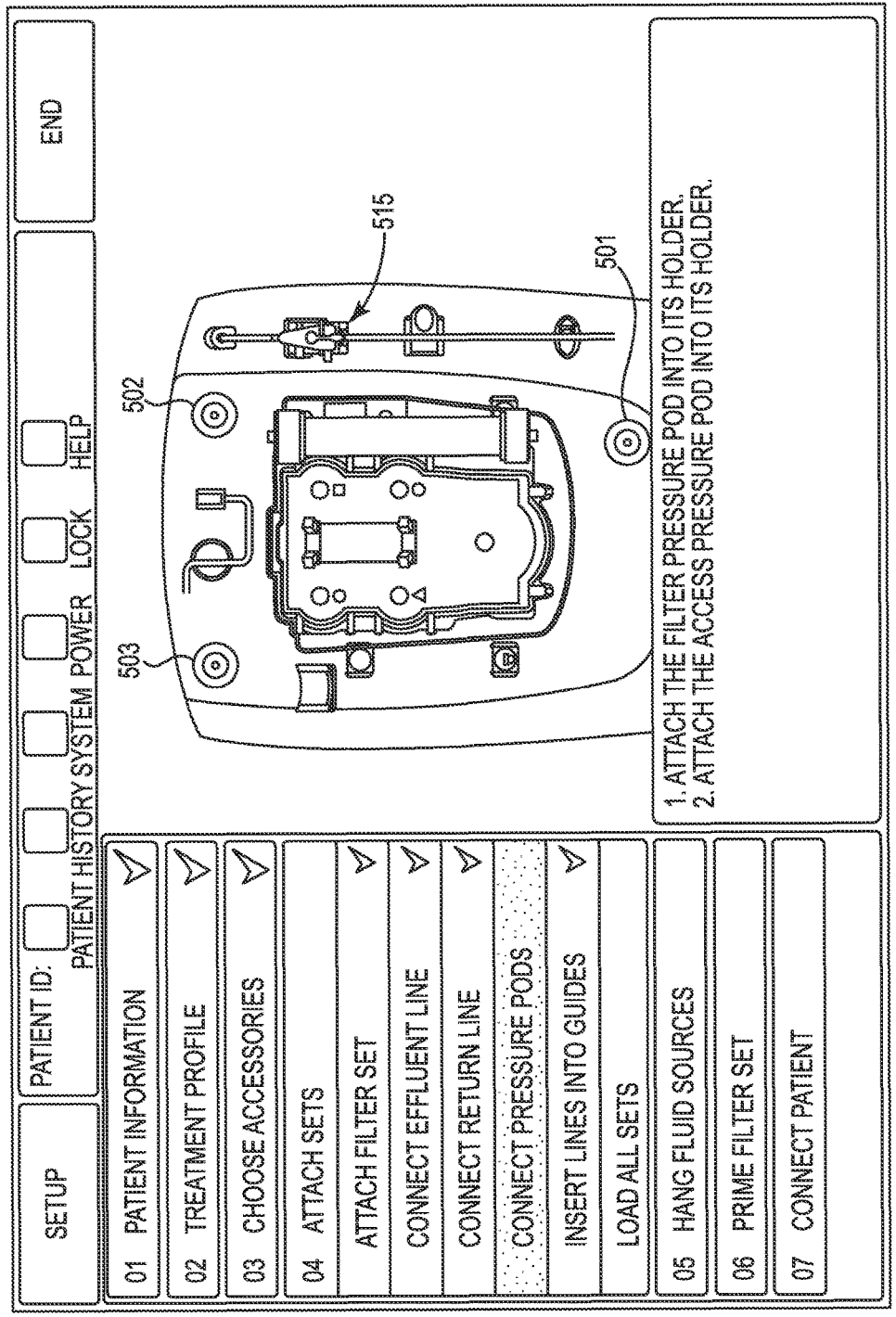
Figure 16D:
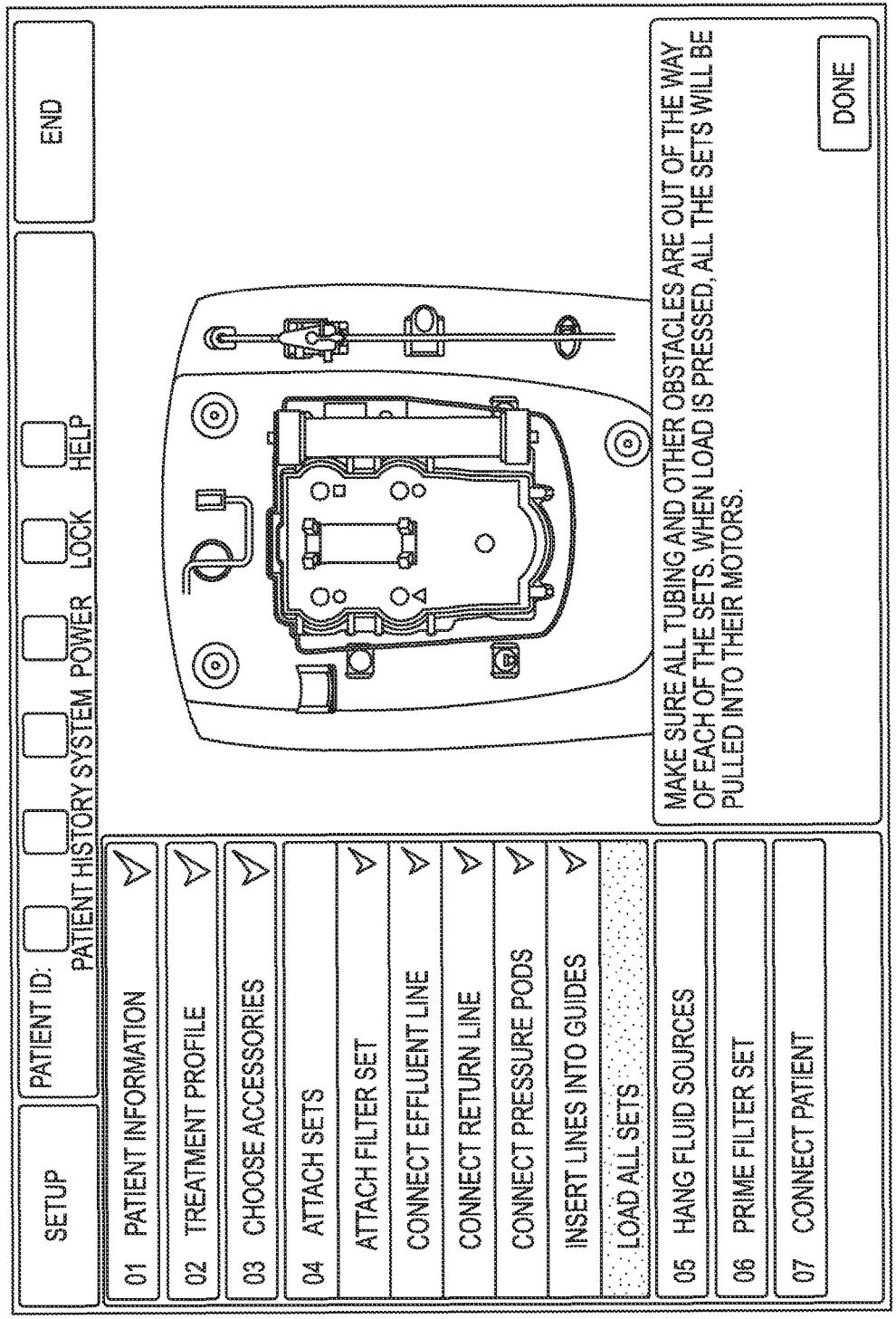

As shown in FIGS. 16A-16D, as various components, such as various pressure pod apparatus and/or open line elements, are properly connected into the system 10, the graphical user interface may provide information instructing the user to connect various components (e.g., visual and textual information) as well as information indicative of the connection of components (e.g., showing components on the display that have been connected). For example, FIG. 16A shows a screenshot prior to connection of access pressure pod (shown later as pod 501) and filter pressure pod (shown later as pod 502) (e.g., as such only the receptacles 512, 513 for receiving such pods is shown), but after connection of effluent pressure pod 503. As shown therein, effluent pressure pod 503 is not highlighted and the connection of effluent pressure pod 503 is shown as being properly completed. The receptacles 512, 513 for filter pressure pod 502 and access pressure pod 501 are highlighted to indicate that such connections have not been made. As shown in FIG. 16B, once the filter pressure pod 502 has been properly connected, it is shown as being connected and is no longer highlighted in the screenshot thereof. Likewise, this screenshot also shows the return monitor line 515 has been properly connected as it is also shown in the screenshot. However, since the access pressure pod 501 has not yet been properly connected, it remains highlighted and only a receptacle 513 is shown. As shown in FIG. 16C, all three pressure pods are shown as no longer being highlighted on the screen shot indicating all the pressure pods 501-503 have been properly connected.

One skilled in the art will recognize that any sort of information indicative of the completion of various tasks may be used to inform the user. For example, highlighting, changing or adding shape or component configurations, text, or any other visual or audio indication of completion of tasks as the sequence of such tasks are completed may be used. Such information indicative of the completion of tasks and instructions on the graphical user interface to perform additional tasks provides an automated sequence for a user to follow without requiring the user to confirm connection of one or more components. Although confirmation of various components may not be necessary in one or more embodiments described herein, a user may be asked to provide input via the graphical user interface at one or more steps in one or more processes (e.g., indicate that a step of a discharge ring being clipped into its holder has been completed, tubing has been positioned properly by the user, etc.).

In one or more embodiments, to determine whether the component including the closed container portion (e.g., pressure pod apparatus 80A-80C) has been operatively connected (block 216), the controller 20 may control provision of air from the air pump apparatus 14 to at least one port of the one or more ports (e.g., a positive air flow to the port) of the connection apparatus (e.g., connection apparatus 84A-84C) and within the closed container portion of the component (e.g., pressure pod apparatus 80A-80C) when mounted on the system housing 11 using the connection apparatus. The air pressure resulting from the provision of air to the at least one port is monitored to determine whether the component including the closed container portion (e.g., pressure pod apparatus 80A-80C) is operatively connected to the system housing 11 based on a detected rise in the monitored pressure.

Further, for example, in one or more embodiments, to detect operative connection of components including closed container portions, generally, a rise in pressure magnitude (whether a negative pressure decreasing further, or a positive pressure increasing) may be used in detecting operative connection of such components. For example, as described above with respect to providing a positive air flow to the port, when the closed container is connected then a pressure increase equatable to a magnitude increase may occur and be detectable for used in determining whether the component is connected. However, likewise, the controller 20 may control the pump to provide air flow in the opposite direction (e.g., negative flow away from the port) using the air pump apparatus 14. The air pressure resulting from the pump running in the opposite manner (than when providing the positive flow) may be monitored to determine whether the component including the closed container portion (e.g., pressure pod apparatus 80A-80C) is operatively connected to the system housing 11 based on a detected rise in the monitored pressure magnitude. For example, when the closed container is connected then a pressure decrease which is equatable to a pressure magnitude increase may occur and be detectable for use in detecting an operatively connected component. The positively provided air flow to the port is primarily used in this description, however, the pump may be run in either direction to determine connection of the component by detecting a change in the magnitude of the pressure (e.g., in the connection path between the port and the pump).

Figure 14:
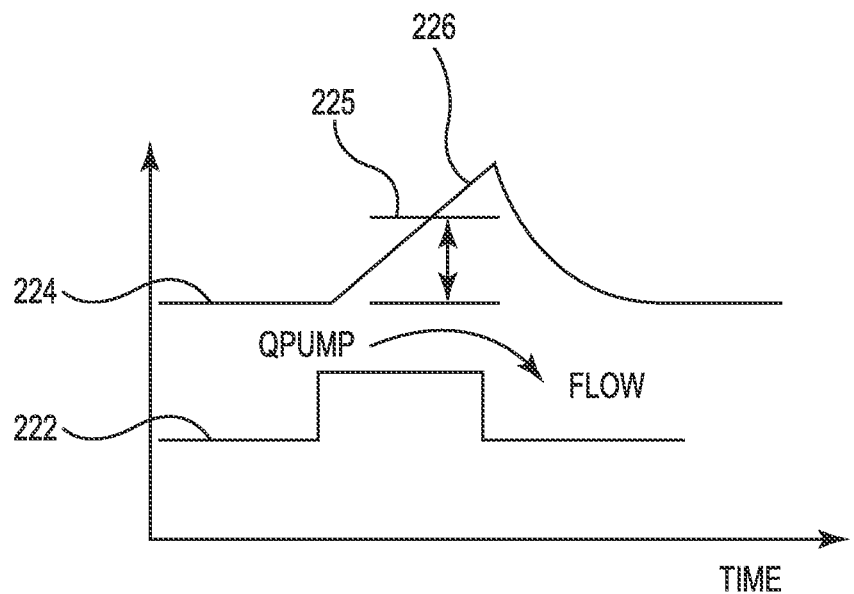
FIG. 14 shows a graph for use in describing the detection of the connection of a component with a closed container portion to a system housing of a system.

As described herein, the process for determining whether a component that includes a closed container portion (e.g., pressure pod apparatus 80A-80C) is connected properly may be different than the process for determining whether an open line element (e.g., return monitor line 82) is connected properly. For example, as shown in FIG. 14, in the case of the component having a closed container portion, since the pressure will only rise if volume is added to the closed container portion when attached, the component connection detection in the case of a closed container portion may be implemented by providing air to the connection point at which the closed container portion is to be mounted (see graph line 222 of FIG. 14). As the pressure (e.g., measured pressure, a pressure that is zeroed out, etc.) (see line 224 of FIG. 14) prior to the provision of such air is known, a rise in pressure (see line 226 of FIG. 14) may be indicative of the proper connection of the component including the closed container portion. For example, in one or more embodiments, if the rise in pressure exceeds a particular threshold (see line 225 in FIG. 14), then it may be determined that a proper connection has been completed. Further, for example, in one or more embodiments, the difference between an initial pressure prior to provision of a volume of air to the connection point and a pressure following provision of such air to the connection point may be used to determine a proper connection (e.g., if such difference exceeds a threshold).

Since a user may attach a component (e.g., pressure pod apparatus 80A-80C) prior to be instructed, it is necessary to be able to detect the presence of such a component if it is already in place before the detection process is started and air is provided to the connection point. For example, one may not be able to rely on the user to follow particular instructions about not attaching a component. To make the detection mechanism sensitive to such a sequencing error by the user, one or more different techniques may be used. For example, the use of a difference between an initial pressure prior to provision of a volume of air to the connection point and a pressure following provision of such air to the connection point may be used to determine a proper connection (e.g., if such difference exceeds a threshold). In other words, the detection may be accomplished by turning on and off air flow to the connection point and making pressure measurements during these two states. For example, the pressure may be measured before the pump is started and measured continuously as it is run. If the pressure rise/difference is used to determine whether the component is properly attached then it does not matter when the component is attached as the difference will indicate the presence of the component. Another process of providing such sensitivity to sequencing error may be to zero out the pressure initially as described in the detailed exemplary embodiment of a particular algorithm provided herein.

Figure 10:
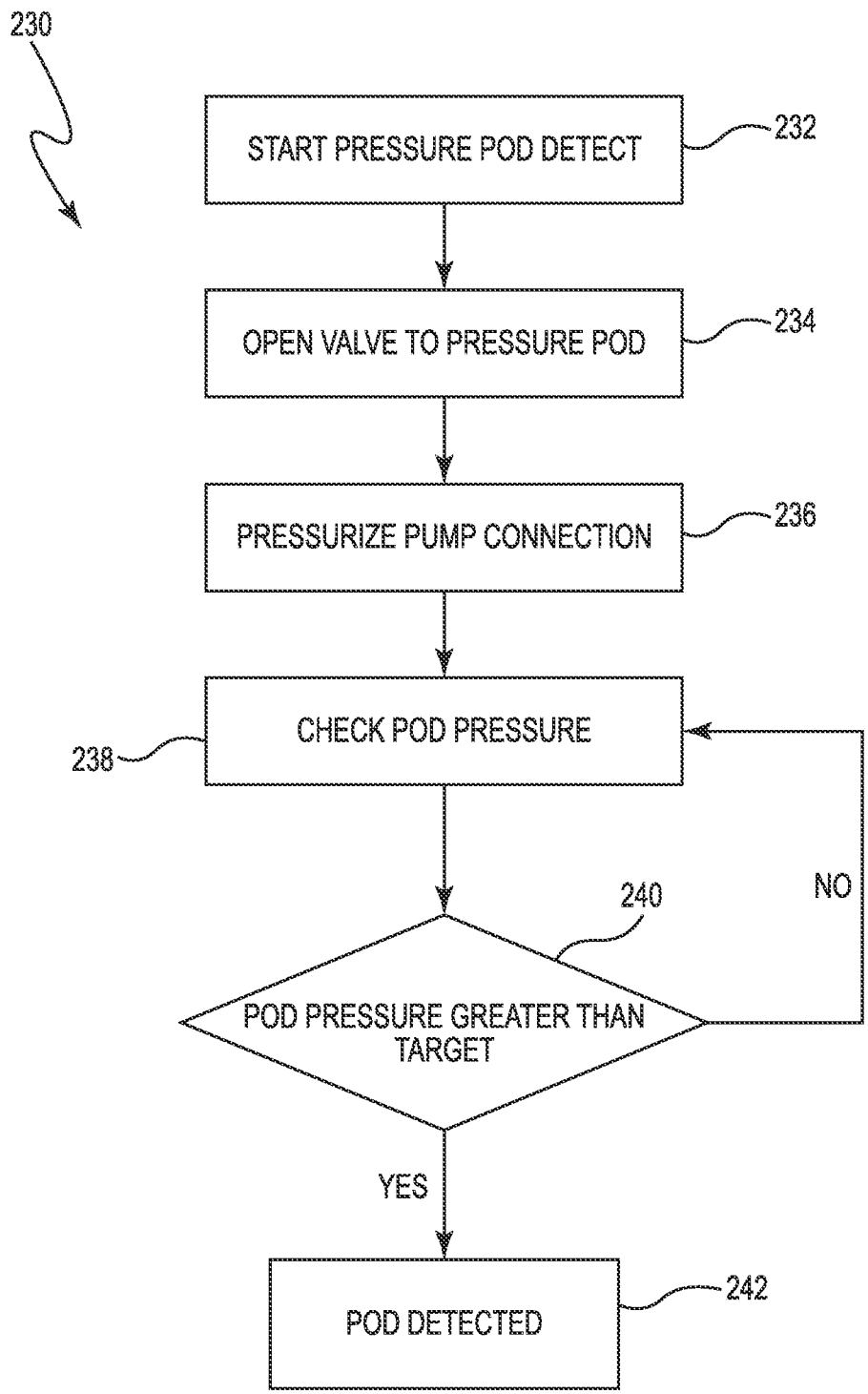
FIG. 10 shows a flow diagram of a more detailed exemplary method of detecting connection of a pressure pod apparatus of an extracorporeal blood set to a system housing of a system.

FIG. 10 shows one exemplary embodiment of a pressure pod apparatus connection detection method 230 described with reference to FIG. 1. For example, after initiation of the pressure pod apparatus connection detection process (block 232), the valve (e.g., one of valves 88A-88C) associated with a particular pressure pod apparatus (e.g., one of pressure pod apparatus 80A-80C) is opened (block 234). Under control of controller 20, the pump apparatus 14 is used to pressurize the connection to the pressure pod apparatus to provide air to within the transducer side air cavity of the pressure pod apparatus (e.g., one of pressure pod apparatus 80A-80C) if mounted on the system housing 11 (block 236). Air pressure resulting from the provision of air to the connection point at which the pressure pod apparatus is to be mounted is monitored (e.g., using a corresponding pressure transducer P1-P3) to detect whether the pressure pod apparatus (e.g., one of pressure pod apparatus 80A-80C) is operatively connected to the system housing 11 based on a detected rise in the monitored pressure.

For example, as described herein, detecting a rise in pressure may include comparing the monitored pressure to a predetermined pressure threshold (block 240) and determining that the pressure pod apparatus is properly connected if such a threshold is exceeded or otherwise satisfied (block 242). For example, in one or more embodiments, a predetermined number of samples of the monitored air pressure satisfy the predetermined threshold may be used to assure that correct connection determination has been made (e.g., eliminating the possibility of measurement error when only a single sample of monitored air pressure is used). In one or more embodiments, if the target threshold is not satisfied, the pressure is continued to be monitored until the pressure pod apparatus is detected, or, for example, a timeout occurs to stop such a detection process.

It will be recognized that only one pressure transducer may be needed to perform the connection detection process provided herein dependent upon the configuration of the system. Further, if the connection detection process is performed with respect to only one component at one connection point, then no valves may be required in such configuration. However, if multiple components are attached at multiple ports, then valves for control of air to the respective connection points (e.g., ports) from the pump apparatus may be required.

Figure 11:
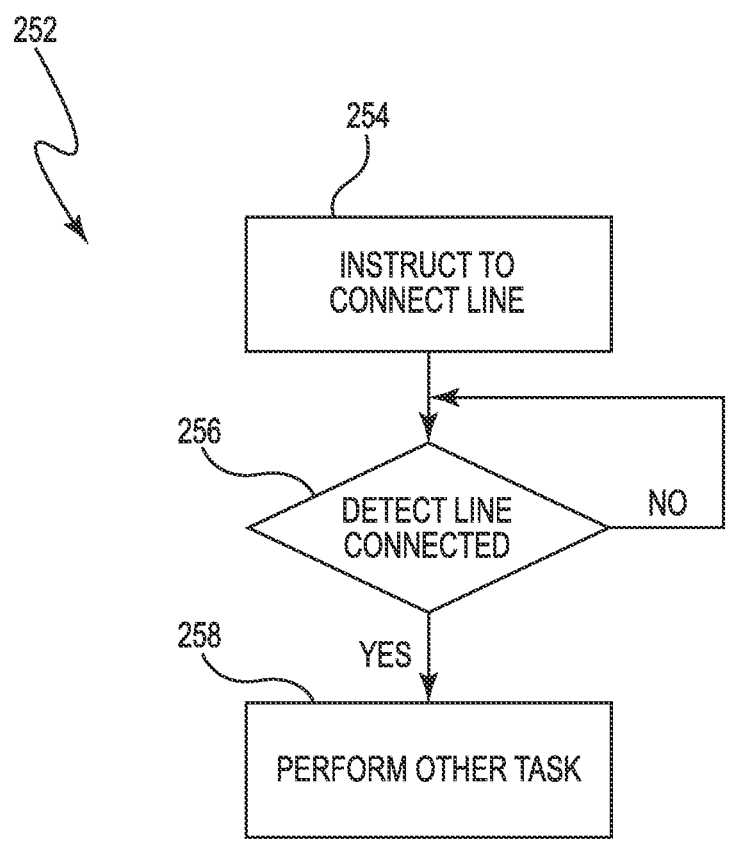
FIG. 11 shows a flow diagram of an exemplary method of connecting an open line element of an extracorporeal blood set to a system housing of a system, for example, such as shown generally in FIGS. 1-3.

FIG. 11 shows an exemplary component connection detection method 252 for connecting one or more open line elements (e.g., return monitor line 82) to a housing 11 of an extracorporeal blood treatment system 10. For example, the detection method 252 may include instructing a user, e.g., via a graphical user interface, to connect an open line element (e.g., return monitor line 82) configured to be mounted on the system housing 11 of the extracorporeal blood treatment system 10 (e.g., using return pressure port) (block 254). For example, although not shown in FIGS. 16A-16D, when the "Connect Return Line" instruction is highlighted on a graphical user interface, the user may be instructed to place the deaeration chamber in its holder and attach the deaeration chamber monitor line to the return pressure port. If the system 10 determines that the open line element has been operatively connected (block 256), the user may be instructed to perform any other task desired (block 258) (e.g., connect another component, such as a pressure pod apparatus, etc.). For example, as shown in FIG. 16B, the user may be instructed to "1. Attach the Filter Pressure Pod into its holder."

In one or more embodiments, to determine whether the open line element (e.g., return monitor line 86) has been operatively connected (block 256), the controller 20 controls injection of air using the air pump apparatus 14 to at least one port of the one or more ports of the connection apparatus (e.g., connection apparatus 86) and within the open line element (e.g., return monitor line 86) when mounted on the system housing 11 using the connection apparatus. The rate of decay of pressure of the injected air is monitored (e.g., using pressure transducer Pline) to determine whether the open line element (e.g., return monitor line 86) is operatively connected to the system housing 11.

Figure 15:
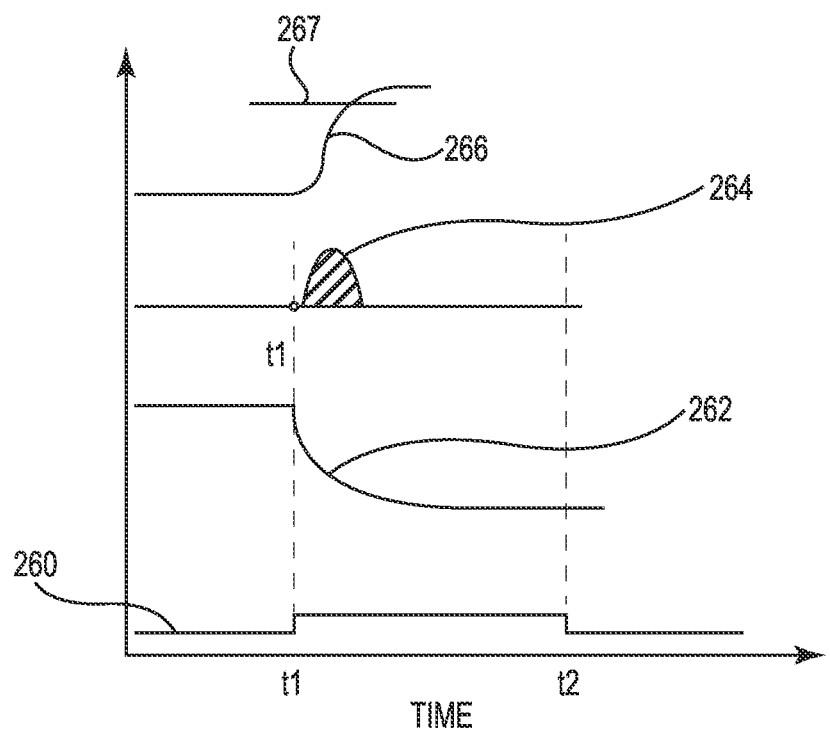
FIG. 15 shows a graph for use in describing the detection of the operative connection of an open line element to a system housing of a system.

For example, as shown in FIG. 15, in the case of the open line element, since a pressure rise may be difficult to detect if volume is added thereto like the method for detecting connection of a closed container portion, a different connection detection technique may be used. As shown in FIG. 15, graph line 260 is representative of the position of a valve (open or closed). The valve is normally closed, but when opened, pressurized air is injected to the connection point to which the open line element is to be connected. As such, as shown by line 262 in FIG. 15, at time t1, when the valve is opened, air is rapidly released and flow is delivered to the connection point. A pressure associated with the connection point is measured. Since the pressure is a function of the resistance and the flow at the connection point, the pressure on the pressurized side of the valve will have an associated rate of decay depending upon whether an open line element is connected at the connection point or whether an open line element is not attached. This pressure rate of decay of the pressurized air is shown by graph line 262 in FIG. 15. It is noted that, at time t1, immediately following the injection of air to the connection point, the pressure is at its peak and thereafter decays. As the released air flows through the connection point, a pressure associated with the connection point is measured as shown by graph line 264 in FIG. 15. The corresponding pressure at the connection point is low initially until the valve is opened at time t1. The pressure at the connection point then rises following the injection of air to the connection point and subsequently decays as the pressure on both sides of the open valve equalize.

In one or more embodiments, as shown in FIG. 15, the pressure shown as line 264 may be integrated by the controller 20 to provide an integral pressure shown as line 266. The integral pressure may be compared to a threshold chosen to distinguish between the rate of decay of the injected air when no open line element is connected versus the rate of decay of the injected air when an open line element has been connected. For example, the integrated pressure may be calculated on the difference between the pressure at the connection point following the injection of air and starting pressure at the connection point prior to injection of air thereto. As such, to determine whether an open line element has been properly connected, the pressure at the connection point is monitored following the injection of air thereto. The monitored pressure is integrated to provide an integral pressure (see graph line 266 of FIG. 15)

(e.g., generally, the pressure integral is monotonically increasing during the integration of the pressure pulse; the integral may stay at a maximum value (equal to the area under the pressure curve) until the test is complete and the algorithm resets the integral to zero in preparation for the next test, or when exiting the final test) for comparison to an integral pressure threshold 267 determined based on, for example, the integration of the pressure pulse when the open line element is not connected versus when the open line element is properly connected. For example, if the monitored integral pressure exceeds the integral pressure threshold 267 it may be determined that an open line element has been properly connected. For example, in one or more embodiments, if multiple samples of the monitored integral pressure exceed the integral pressure threshold, a proper connection may be indicated.

Figure 12:
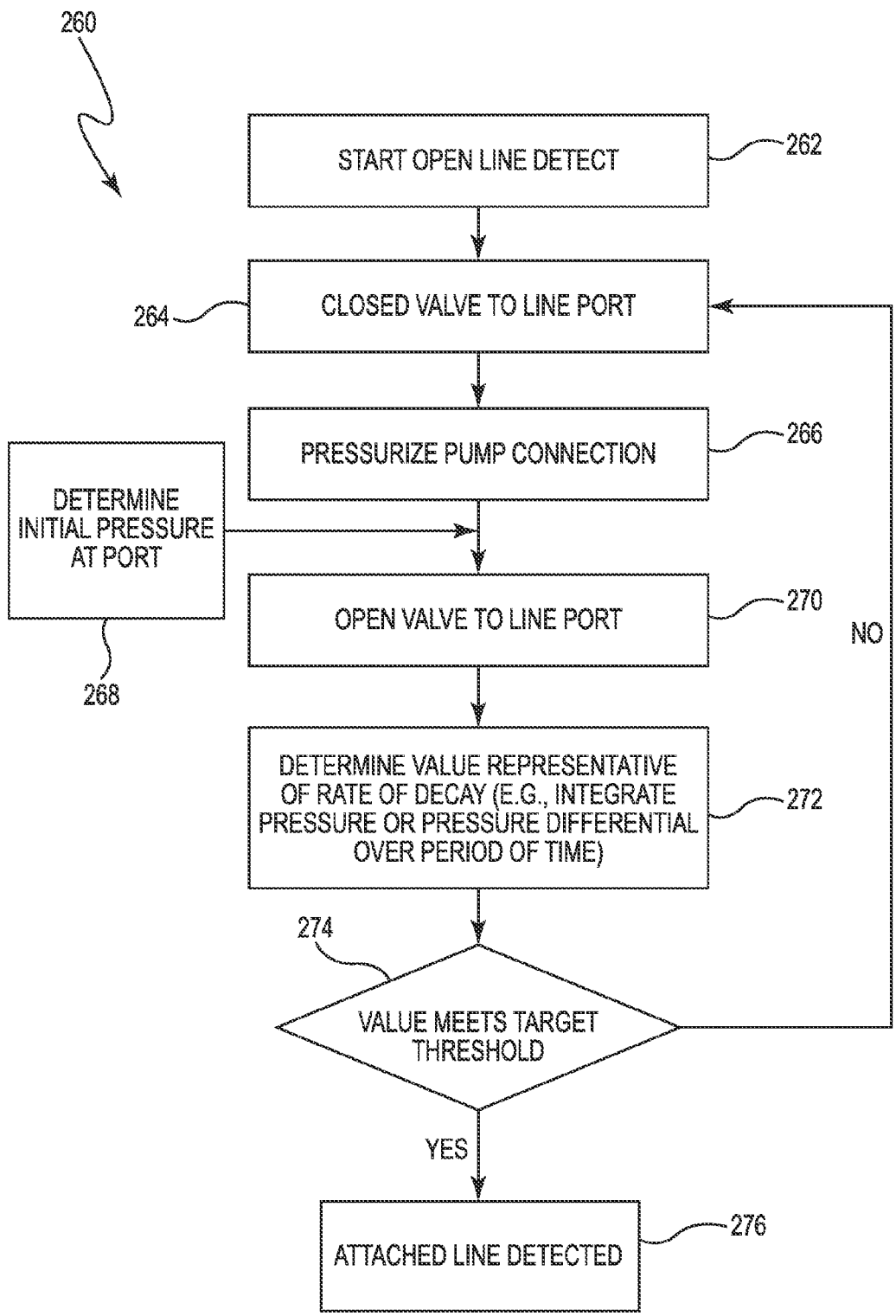
FIG. 12 shows a flow diagram of a more detailed exemplary method of detecting connection of an open line element of an extracorporeal blood set to a system housing of a system.

FIG. 12 shows one exemplary embodiment of a return monitoring line connection detection method 260 described with reference to FIG. 1. For example, after initiation of the monitor line connection detection process (block 232), the valve 90 associated with return port 86 is closed (block 264) via switch Sline. The pump apparatus 14 is controlled by controller 20 (e.g., via feedback from transducer Ppump) to pressurize the connection between pump apparatus 14 and valve 90 (block 266). For example, with the valve 90 closed, the pump apparatus may be driven such that the pressure measured between the pump apparatus 14 and the valve 90 by pressure transducer Ppump is large enough to provide an adequate rate of decay to determine the connection of the return monitor line 82.

With the initial pressure at the return port 86 known from measurements by the pressure transducer Pline (block 268), the valve 90 is opened to inject air to the return port 86 (block 270). If the return monitor line 82 is connected such pressurized air will be provided therein. Air pressure resulting from the provision of air to the return port 86 at which the return monitor line 82 is to be mounted is monitored (e.g., using pressure transducer Pline) to detect whether the monitor line 82 is operatively connected to the system housing 11 based on the rate of decay as described herein. For example, as described herein, a value representative of the rate of decay of the injected air is determined (block 272). In one or more embodiments, such a value may be determined by integrating the pressure monitored by pressure transducer Pline and/or the pressure differential between the pressure at the return port 86 after the injection of air and the pressure of the return port 86 prior to the injection of air. Such integration may be over a predetermined time period after the injection of air.

The value representative of the rate of decay may be compared to a threshold (block 274). If the value representative of the rate of decay (e.g., the integral pressure) meets the target threshold (e.g., an integral pressure threshold), it may be determined that the monitor line 82 is properly attached to the return port 86. If the threshold is not met, the process may be repeated until attachment of the monitor line 82 is detected, and/or until a timeout process occurs. One or more further thresholds may be used to indicate one or more other detected conditions. For example, in addition to injecting pressurized air into the return line port and determining that the return line is connected if the return line pressure integral is above a threshold value, another threshold (e.g., a higher value threshold; significantly higher relative to the prior threshold) may be used to sense that the return line is not only connected but that the liquid barrier between the dearation chamber and the return pressure port is occluded (e.g., wet). For example, instead of just indicating that the return line is or is not connected, the algorithm may also detect an additional possibility relating to the liquid barrier.

Figure 13:
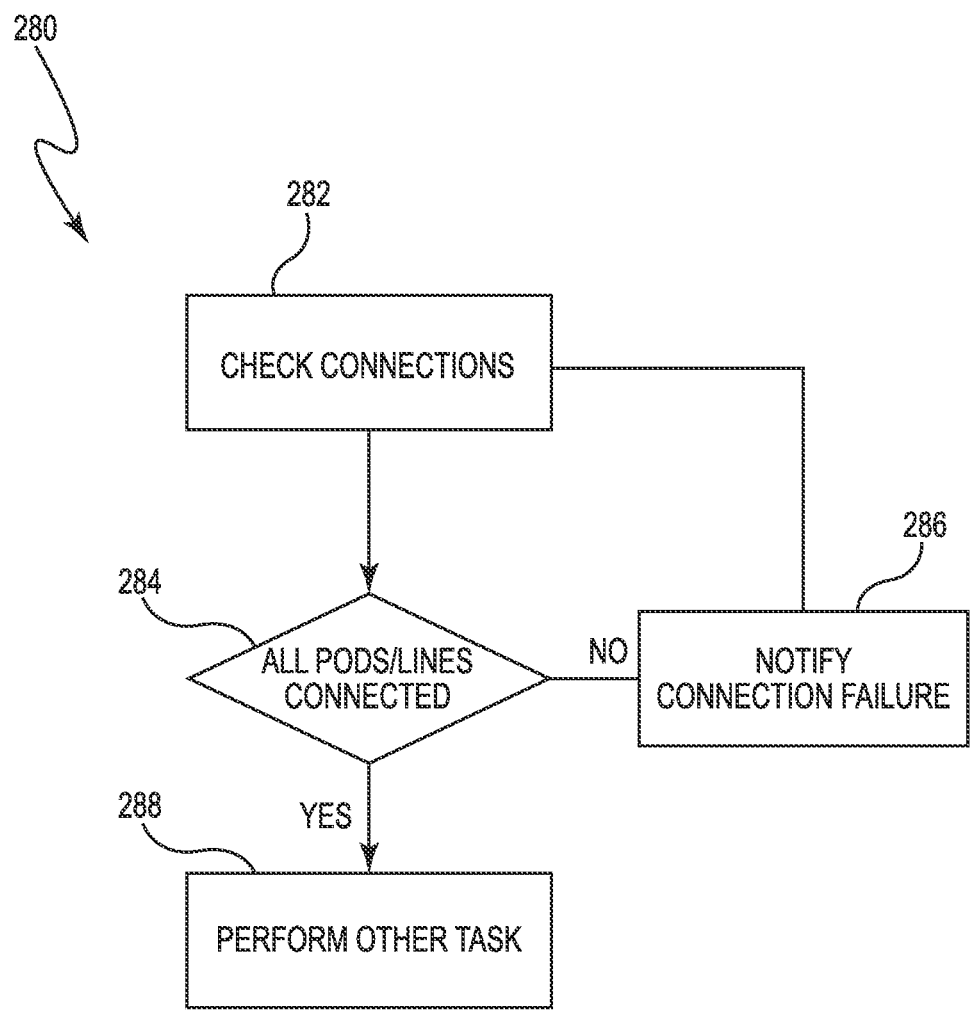
FIG. 13 shows a flow diagram of another exemplary method of connecting components of an extracorporeal blood set to a system housing of a system, for example, such as shown generally in FIGS. 1-3.

FIG. 13 shows a flow diagram of another exemplary method of connecting components of an extracorporeal blood set to a system housing of a system, for example, such as shown generally in FIGS. 1-3. For example, during system setup prior to performing treatment, the system will guide a user through the connection of necessary components to the system including, for example, pressure pod apparatus, monitor lines, etc., as described herein. At one point in time or another during such setup, the controller 20 of the system 10 may implement method 280. The method 280 includes checking (e.g., sequentially and/or in any order) whether a predetermined number of components, such as the pressure pod apparatus and monitor line, are properly connected (block 282). This may be accomplished, for example, by repeating connection detection processes as described herein and/or by checking changed states or other indicators set by the controller based on previous connection detection processes carried out that detected connection of such various components. If the predetermined number of components are not detected as being connected within a period of time (block 284), then a notification indicating such connection failure may be issued (e.g., an audible or visual alarm) (block 286). If the predetermined number of components are indicated as being connected, then the system may provide instructions to a user to perform other tasks (block 288).

One exemplary component connection detection algorithm for connecting pressure pod apparatus and a return monitor line shall be described with reference to FIG. 1. For example, such an implementation may be carried out by sampling pressure readings at 60 Hz (1/60 sec time intervals) and executing the following exemplary steps. However, although the implementation presented may use 60 Hz pressure samples, the connection detection algorithm may be implemented using other sample rates as dictated by alternate system architectures and pressure dynamics.

Step 1—For each pressure pod apparatus 80A-80C and return pressure port 86 to be verified, set the state of the component to unconnected. Run pump 14 (e.g., ARPS pump) to zero pressure (as measured by transducer Ppump) with pressure pod valves 88A-88C (e.g., valves in connection with pump 14) opened (e.g., simultaneously) for all pressure pod apparatus 80A-80C installations to be verified listed on a "pod to detect list" (e.g., an effluent pressure pod, a filter pressure pod, an access pressure pod and a return line of a disposable set). If the pressure cannot be zeroed within a predetermined time, then a detection failure indication is sent to the graphical user interface, and the detection algorithm is terminated. The return monitor line valve 90 (e.g., solenoid valve) remains closed for Step 1. Pressure pod valves 88A-88C are closed after pressure is zeroed.

Step 2—Determine the first pressure pod apparatus 80A-80C or return monitor line 82 to be detected from the "pod to detect list" input (e.g., an input list of components whose connections are to be verified), or the next pod in the list on subsequent executions of this step.

Step 3—If detecting connection of a pressure pod apparatus 80A-80C, proceed with Steps 4-6. If detecting connection of a return monitor line 82 skip to Step 7.

Step 4—(Pressure Pod Apparatus Connection Detection)—Open pressure pod valve (e.g., 88A-88C) for corresponding pressure pod apparatus (e.g., 80A-80C) to be verified and start pump apparatus 14 in pressure control mode with, for example, a pressure target of 50 mmHg.

Step 5—(Pressure Pod Apparatus Connection Detection)—After a short wait time (e.g., 0.5 seconds), check to see if the pressure associated with the pod apparatus to be verified is above a threshold (e.g., 15 mmHg). If the pressure pod apparatus being verified is not installed, then the pressure will remain below threshold.

Step 6—(Pressure Pod Apparatus Connection Detection)—When the pressure for the pressure pod apparatus to be verified is above the threshold for a particular number of samples (e.g., 16 out of 20 samples or 10 sequential samples), then connection of the pressure pod in operative condition is verified. For example, the pressure pod connection detection algorithm may be repeated until the pressure pod apparatus is verified or the algorithm is timed out. For example, the algorithm may make 4 attempts to detect the pressure pod apparatus over a 30 second time frame before moving on and/or issuing a failure. Skip then to Step 14.

Step 7—(Monitor Line Detection)—To detect connection of a monitor line 82 proceed with Steps 8-13.

Step 8—(Monitor Line Detection)—With all pressure pod valves 88A-88C for corresponding pressure pod apparatus 80A-80C and return monitor line valve 90 closed, the pump apparatus 14 in pressure control mode is driven to achieve a target pressurization as measured by transducer Ppump of, for example, 320 mmHg at the pump apparatus outlet. In other words, in at least one embodiment, the air line between the pump apparatus 14 and the valve 90 associated with return pressure port 86 is being pressurized.

Step 9—(Monitor Line Detection)—When the pressure as measured by transducer Ppump has almost reached the target pressurization (e.g., 300 mmHg for a target of 320 mmHg) and while the valves remain closed, an average return port pressure is determined (e.g., using measurements by transducer Ppump). This determines an offset on the unpressurized return port 86 as valve 90 has not yet been opened. In other words, a starting pressure is determined.

Step 10—(Monitor Line Detection)—Stop the pump apparatus 14 by disabling the pump pressure control and open the valve 90 (via switch Sline) associated with the return monitor port 86 (e.g., the valve 90 being between the pump apparatus 14 and the return pressure port 86). This will cause a return pressure pulse resulting from the release of the pressurized air in the line between the pump apparatus 14 and the valve 90 associated with return pressure port 86.

Step 11—(Monitor Line Detection)—For a predetermined period of time (e.g., about 1 second) after opening the valve 90, calculate the time integral of the difference between the pressure at the return pressure port 86 as measured by pressure transducer Pline associated therewith and the average return port pressure reading (e.g., the starting pressure) as measured earlier in Step 9 (e.g., a value representative of the rate of decay of the pressurized air injected). For example, the sample rate of the return pressure readings should be sufficiently fast to accurately characterize the dynamics of the pressure pulse rise and decay (e.g., 60 Hz).

Step 12—(Monitor Line Detection)—If after the predetermined time (e.g., 1 second), the return port pressure integral from Step 11 is equal to or greater than a predetermined integral threshold, then the connection of the monitor line (e.g., the return monitor line of a disposable set) to the return pressure port 86 is verified as being proper and the return monitor line detection is complete. In other words, the connection of the monitor line 82 causes the pressure pulse to decay more slowly, thus increasing the final value of the pressure integral. The integral threshold may be determined using prototype hardware by repeating, for example, Steps 8-11, multiple times with and without the return line connected. For example, in one embodiment, the detection integral threshold may be determined to be 9 mmHg-sec. Further, for example, in one embodiment, a typical return pressure integral value after 1 second with a return monitor line attached may be determined to be 12.23 mmHG-sec.

Step 13—(Monitor Line Detection)—If after the predetermined time (e.g., 1 second), the return port pressure integral from Step 11 is less than a predetermined threshold integral, then the connection of the monitor line (e.g., the return monitor line of a disposable set) to the return pressure port 86 is NOT verified as being proper and the return monitor line detection may either be terminated or repeated as many times as desired for a particular application. In other words, the absence of the return line causes the pressure pulse to decay more quickly, resulting in the final value of the pressure integral being significantly less than it is when the return monitor line is connected. For example, in one embodiment, a typical return pressure integral value after 1 second with a return monitor line not attached may be determined to be 5.93 mmHG-sec.

Step 14—If the connection detection tests for all pressure pod apparatus or return monitor lines from the "pod to detect list" input have been verified as being connected properly (e.g., states set by controller indicating proper connection), continue to Step 15, otherwise go back to Step 2 to attempt connection detection of the next pod apparatus or monitor line in the "pod to detect list" input. For example, the components whose connection is to be detected according to the connection detection algorithm are listed as input components and the connection detection algorithm may sequentially and/or in any order run through such components for verification of connection. For example, pressure pod connection detection may be performed to detect connection of an effluent pressure pod, a filter pressure pod, and an access pressure pod and monitor line detection may be performed for a return monitor line; however, the order in which such detections occur may vary depending upon the application to be implemented. The present disclosure is not limited to any particular time sequence for carrying out such detection processes, although one or more time sequence may be beneficial over others.

Step 15—Open all pressure pod valves 88A-88C corresponding to pressure pod apparatus 80A-80C verified and run pump apparatus 14 to zero as measured by transducer Ppump (e.g., which may be verified by pod transducers P1-P3). Return monitor line valve 90 remains closed (e.g., return monitor line pressure is not driven to zero). In at least one embodiment, if all the pressure pod apparatus and/or monitor lines are not detected within a timeout period of time, then the connection detection algorithm may set a "pod detection failure" flag and terminate the connection detection algorithm.

Step 16—Close all pressure pod valves 88A-88C corresponding to pressure pod apparatus 80A-80C and terminate connection detection algorithm.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An extracorporeal blood treatment system comprising:
an air pump apparatus;
one or more pressure transducers;
a controller operatively coupled to the air pump apparatus and the one or more pressure transducers;
a system housing to contain at least the air pump apparatus, the controller, and the one or more pressure transducers; and
an extracorporeal blood set comprising a plurality of components configured to be mounted on the system housing of the extracorporeal blood treatment system using connection apparatus, wherein the connection apparatus comprises one or more ports to connect the one or more pressure transducers contained in the system housing to one or more components of the plurality of components of the extracorporeal blood set when mounted on the system housing, wherein the controller is configured to:
control the air pump apparatus to provide air to at least one port of the one or more ports and within at least a portion of one or more components when mounted on the system housing using the connection apparatus; and
monitor air pressure resulting from the provision of air to the at least one port using at least one of the one or more pressure transducers to detect whether one or more components of the plurality of components are operatively connected to the system housing.

2. The system of claim 1, wherein the extracorporeal blood set comprises one or more components comprising a closed container portion mountable on the system housing of the extracorporeal blood treatment system, wherein the closed container portion is operatively connectable to at least one of the one or more pressure transducers, and further wherein the controller is configured to:
control provision of air from the air pump apparatus to at least one port of the one or more ports and within the closed container portion of at least one component when mounted on the system housing using the connection apparatus, wherein the at least one component creates an increase in resistance to the air provided when mounted on the system housing; and
monitor air pressure resulting from the provision of air to the at least one port to determine whether the component comprising the closed container portion is operatively connected to the system housing based on a detected rise in the monitored pressure due to the increased resistance.

3. The system of claim 1, wherein the extracorporeal blood set comprises a plurality of pressure measurement apparatus configured to be mounted on the system housing of the extracorporeal blood treatment system, wherein each of the plurality of pressure measurement apparatus comprises a pressure pod body configured to be mounted on the system housing and a diaphragm separating a fluid side cavity and a transducer side air cavity, wherein the transducer side air cavity is operatively connectable to at least one of the one or more pressure transducers such that pressure of fluid when present in the fluid side cavity is transferred to the transducer side air cavity via the diaphragm and measureable using the at least one pressure transducer, and further wherein the controller is configured to:
control provision of air from the air pump apparatus to at least one port of the one or more ports and into the transducer side air cavity of a first pressure measurement apparatus of the plurality of pressure measurement apparatus when mounted on the system housing; and
monitor air pressure resulting from the provision of air to the at least one port to detect whether the first measurement apparatus is operatively connected to the system housing based on a detected rise in the monitored pressure.

4. The system of claim 3, wherein the controller is configured to detect a rise in pressure by comparing the resulting air pressure to a predetermined pressure threshold and determining that the first pressure measurement apparatus is operatively connected if a predetermined number of samples thereof satisfy the predetermined pressure threshold.

5. The system of claim 3, wherein the controller is configured to detect a rise in pressure by monitoring pressure at the at least one port prior to and after providing air thereto to detect a pressure difference.

6. The system of claim 1, wherein the extracorporeal blood set comprises an open line element configured to be mounted on the system housing of the extracorporeal blood treatment system and connectable to a port of the one or more ports of the connection apparatus, wherein the open line element is operatively connected to at least one of the one or more pressure transducers when mounted on the system housing, and further wherein the controller is configured to:
control injection of air to the port of the one or more ports using the air pump apparatus and within the open line element when mounted on the system housing, wherein the open line element creates an increase in resistance to the injected air when mounted on the system housing resulting in a decreased rate of decay of the pressure of the injected air; and
monitor a rate of decay of pressure of the injected air to determine whether the open line element is operatively connected to the system housing.

7. The system of claim 6, wherein the controller is further configured to monitor the rate of decay of pressure by:
determining a pressure difference integral of the injected air over a period of time following the injection of pressurized air to the port by integrating a difference between the pressure when air is being injected to the port and an initial pressure prior to air being injected to the port;
comparing the pressure difference integral to a predetermined pressure integral threshold; and
detecting that the open line element is operatively connected if the pressure difference integral satisfies the predetermined pressure integral threshold.

8. An extracorporeal blood treatment system comprising:
an air pump apparatus;
one or more pressure transducers;
a controller operatively coupled to the air pump apparatus and the one or more pressure transducers;
a system housing to contain at least the air pump apparatus, the controller, and the one or more pressure transducers; and
an extracorporeal blood set comprising a plurality of components, wherein the plurality of components comprise a plurality of pressure measurement apparatus configured to be mounted on the system housing of the extracorporeal blood treatment system, wherein each of the plurality of pressure measurement apparatus comprises a pressure pod body configured to be mounted on the system housing and a diaphragm separating a fluid side cavity and a transducer side air cavity, wherein the transducer side air cavity is operatively connectable to at least one of the one or more pressure transducers such that pressure of fluid when present in the fluid side cavity is transferred to the transducer side air cavity via the diaphragm and measureable using the at least one pressure transducer, wherein the controller is configured to:

control the air pump apparatus to provide a positive air flow from the air pump apparatus to at least one port of the one or more ports into the transducer side air cavity of a pressure measurement apparatus of the plurality of pressure measurement apparatus when mounted on the system housing or provide a negative air flow from at least one port of the one or more ports opposite the positive air flow; and monitor air pressure resulting from the provision of air by the air pump to detect whether the pressure measurement apparatus is operatively connected to the system housing based on a detected change in the pressure magnitude.

9. The system of claim 1, wherein the system further comprises a clarifying air filter connected between the air pump apparatus and the one or more ports.

10. The system of claim 1, wherein the system further comprises a plurality of valves, and further wherein the controller is configured to operate a different valve for each component of the plurality of components to be mounted on the system housing to allow air from the air pump apparatus to be provided for use in detecting whether each respective component of the plurality of components to be mounted has been operatively connected.

11. The system of claim 1, wherein the plurality of components of the extracorporeal blood set comprises at least a predetermined number of pressure measurement apparatus to be operatively connected to the one or more pressure transducers, and further wherein the controller is further configured to:

detect, during a period of time, whether each of the predetermined number of pressure measurement apparatus has been operatively connected; and alert a user if all of the predetermined number of pressure measurement apparatus have not been operatively connected during the period of time.

12. The system of claim 1, wherein the system further comprises a user interface, and wherein the controller is further configured to automatically instruct a user, via the user interface, to perform another task upon detecting that a first component of the one or more components is operatively connected.

13. The system of claim 12, wherein the controller is further configured to automatically instruct a user, via the user interface, to attach one or more additional components of the plurality of components and, respectively, detect whether each of the one or more additional components are operatively connected to the system housing upon detecting that a first component of the one or more components is operatively connected.

14. A method of connecting one or more components of an extracorporeal blood set to a housing of an extracorporeal blood treatment system, wherein the system housing contains one or more pressure transducers and an air pump apparatus, and further wherein the system comprises connection apparatus comprising one or more ports to connect the one or more pressure transducers to the one or more components of the extracorporeal blood set, wherein the method comprises:

providing an extracorporeal blood set comprising a plurality of components configured to be mounted on the system housing of the extracorporeal blood treatment system;

instructing a user, via a user interface, to connect a first component of the plurality of components;

providing air generated by the air pump apparatus to at least one of the one or more ports for use in determining whether the first component is operatively connected to the system housing via the at least one port such that a pressure associated with the first component is measureable using at least one of the one or more pressure transducers; and automatically instructing a user, via the user interface, to perform another task upon detecting that the first component is operatively connected.

15. The method of claim 14, wherein providing the extracorporeal blood set comprises providing one or more components comprising a closed container portion mountable on the system housing of the extracorporeal blood treatment system, wherein the closed container portion is operatively connectable to at least one of the one or more pressure transducers, and further wherein providing air generated by the air pump apparatus comprises:

controlling provision of air from the air pump apparatus to at least one port of the one or more ports and within the closed container portion of at least one component when mounted on the system housing using the connection apparatus; and monitoring air pressure resulting from the provision of air to the at least one port to determine whether the component comprising the closed container portion is operatively connected to the system housing based on a detected rise in the monitored pressure.

16. The method of claim 14, wherein providing an extracorporeal blood set comprising a plurality of components comprises providing an extracorporeal blood set comprising a plurality of pressure measurement apparatus configured to be mounted on the system housing of the extracorporeal blood treatment system, wherein each of the plurality of pressure measurement apparatus comprises a pressure pod body configured to be mounted on the system housing and a diaphragm separating a fluid side cavity and a transducer side air cavity, wherein the transducer side air cavity is operatively connectable to at least one pressure transducer of the one or more pressure transducers such that pressure of fluid when present in the fluid side cavity is transferred to the transducer side air cavity via the diaphragm and measureable using the at least one pressure transducer, and further wherein providing air generated by the air pump apparatus for use in determining whether the first component is operatively connected to the system housing comprises:

providing air from the air pump apparatus to at least one port of the one or more ports and into the transducer side air cavity of a first pressure measurement apparatus of the plurality of pressure measurement apparatus when mounted on the system housing; and monitoring air pressure resulting from the provision of air to the at least one port to detect whether the first measurement apparatus is operatively connected to the system housing based on a detected rise in the monitored pressure.

17. The method of claim 14, wherein determining whether the first component is operatively connected to the system housing comprises detecting a rise in pressure if the first component is operatively connected to the system housing, wherein detecting a rise in pressure if the first component is operatively connected to the system housing comprises:

comparing the pressure to a predetermined pressure threshold; and determining that the first component is operatively connected if a predetermined number of samples of the resulting air pressure satisfy the predetermined pressure threshold.

18. The method of claim 14, wherein providing an extracorporeal blood set comprises providing a predetermined number of components to be operatively connected to the system housing, and further wherein the method comprises:

detecting, during a period of time, whether each of the predetermined number of components have been operatively connected; and alerting a user if all of the predetermined number of components have not been operatively connected during the period of time.

19. The method of claim 14, wherein providing the extracorporeal blood set comprises providing an open line element configured to be mounted on the system housing of the extracorporeal blood treatment system and connectable to a port of the one or more ports of the connection apparatus, wherein the open line element is operatively connected to at least one of the one or more pressure transducers when mounted on the system housing, and further wherein providing air generated by the air pump apparatus comprises:

controlling injection of air to the port of the one or more ports using the air pump apparatus and within the open line element when mounted on the system housing; and monitoring a rate of decay of pressure of the injected air to determine whether the open line element is operatively connected to the system housing.

20. The method of claim 19, wherein monitoring a rate of decay of pressure of the injected air comprises:

determining a pressure difference integral of the injected air over a period of time following the injection of pressurized air to the port;

comparing the pressure difference integral to a predetermined pressure integral threshold; and detecting that the open line element is operatively connected if the pressure difference integral satisfies the predetermined pressure integral threshold.

21. The method of claim 14, wherein automatically instructing a user, via the user interface, to perform another task comprises instructing a user, via a user interface, to attach one or more additional components of the plurality of components and, respectively, determine whether each of the one or more additional components are operatively connected.

22. The method of claim 14, wherein automatically instructing a user, via the user interface, to perform another task comprises automatically instructing a user, via the user interface, to perform another task upon detecting that the first component is operatively connected without requiring a user to confirm, via the user interface, that the first component is operatively connected.

23. The method of claim 14, wherein the method further comprises operating a different valve for each component of the plurality of components to be mounted on the system housing to allow air from the air pump apparatus to be used for determining whether each respective component of the plurality of components to be mounted has been operatively connected.

24. A method of connecting one or more pressure measurement apparatus of an extracorporeal blood set to a housing of an extracorporeal system, wherein the system housing contains one or more pressure transducers and an air pump apparatus, and further wherein the system comprises connection apparatus comprising one or more ports to connect the one or more pressure transducers to the one or more pressure measurement apparatus of the extracorporeal blood set, wherein the method comprises:

providing one or more pressure measurement apparatus of an extracorporeal blood set, wherein each of the one or more pressure measurement apparatus comprises a pressure pod body configured to be mounted on the system housing and a diaphragm separating a fluid side cavity and a transducer side air cavity, wherein the transducer side air cavity is operatively connectable to at least one pressure transducer of the one or more pressure transducers such that pressure of fluid when present in the fluid side cavity is transferred to the transducer side air cavity via the diaphragm and measureable by the at least one pressure transducer;

providing air generated by the air pump apparatus to a port of the one or more ports and into the transducer side air cavity of a first pressure measurement apparatus when mounted on the system housing; and monitoring air pressure resulting from the provision of air to the port to detect whether the first pressure measurement apparatus is operatively connected to the system housing based on a detected rise in the monitored pressure.

25. The method of claim 24, wherein detecting a rise in the monitored pressure comprises:

comparing the pressure to a predetermined pressure threshold; and determining that the pressure measurement apparatus is operatively connected if a predetermined number of samples of the pressure satisfy the predetermined pressure threshold.

26. The method of claim 24, wherein the method further comprises automatically instructing a user, via a user interface, to attach one or more additional pressure measurement apparatus of the one or more pressure measurement apparatus if the first pressure measurement apparatus is operatively connected, and, respectively, determine whether the one or more additional pressure measurement apparatus are operatively connected.

27. The method of claim 26, wherein automatically instructing a user, via the user interface, to attach one or more additional pressure measurement apparatus is performed without requiring a user to confirm, via the user interface, that the first pressure measurement apparatus is operatively connected.

28. The method of claim 24, wherein the method further comprises operating a different valve for each of the one or more pressure measurement apparatus to allow provision of air from the air pump apparatus to be used for determining whether the respective pressure measurement apparatus has been operatively commented.

29. The method of claim 24, wherein providing the one or more pressure measurement apparatus comprises providing a predetermined number of pressure measurement apparatus to be operatively connected, and further wherein the method comprises: detecting, during a period of time, whether each of the predetermined number of pressure measurement apparatus have been operatively connected; and alerting a user if all of the predetermined number of pressure measurement apparatus have not been operatively connected during the period of time.

30. A method of connecting an open line element of an extracorporeal blood set to a housing of an extracorporeal system, wherein the system housing contains one or more pressure transducers and an air pump apparatus, and further wherein the system comprises connection apparatus comprising at least one port to connect the open line element to at least one pressure transducer of the one or more pressure transducers, wherein the method comprises:
   providing at least one open line element configured to be mounted on the system housing, wherein the open line element is operatively connectable to at least one pressure transducer of the one or more pressure transducers such that a pressure therein is measureable using the at least one pressure transducer;
   controlling injection of pressurized air to the at least one port of the one or more ports using the air pump apparatus and within the open line element when mounted on the system housing; and
   monitoring a rate of decay of pressure of the injected air to determine whether the open line element is operatively connected to the system housing.

31. The method of claim 30, wherein monitoring a rate of decay of pressure of the injected air comprises:
   determining a pressure difference integral of the injected air over a period of time following the injection of pressurized air to the port;
   comparing the pressure difference integral to a predetermined pressure integral threshold; and
   detecting that the open line element is operatively connected if the pressure difference integral satisfies the predetermined pressure integral threshold.

32. The method of claim 31, wherein controlling injection of pressurized air to the at least one port comprises:
   closing a valve in a line to the at least one port to increase pressure in the line; and
   opening the valve to release pressurized air through the at least one port.

33. The method of claim 32, wherein determining the pressure difference integral comprises integrating the difference between the pressure of air through the port upon release of the pressurized air therethrough and an initial pressure value at the port prior to release of the pressurized air.

34. The method of claim 30, wherein the method further comprises automatically instructing a user, via a user interface, to perform one or more additional tasks if the open line element is operatively connected, without requiring a user to confirm, via the user interface, that the open line element is operatively connected.

* * * * *